(12) United States Patent
Nakanishi et al.

(10) Patent No.: US 9,883,673 B2
(45) Date of Patent: *Feb. 6, 2018

(54) METHOD FOR PRODUCING PEST CONTROL AGENT

(71) Applicant: MEIJI SEIKA PHARMA CO., LTD., Chuo-ku, Tokyo (JP)

(72) Inventors: Nozomu Nakanishi, Yokohama (JP); Yoshimasa Fukuda, Yokohama (JP); Shigeki Kitsuda, Yokohama (JP); Ikuya Ohno, Yokohama (JP)

(73) Assignee: MEIJI SEIKA PHARMA CO., LTD., Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 15/141,960

(22) Filed: Apr. 29, 2016

(65) Prior Publication Data

US 2016/0242415 A1 Aug. 25, 2016

Related U.S. Application Data

(62) Division of application No. 14/238,299, filed as application No. PCT/JP2012/071399 on Aug. 24, 2012, now Pat. No. 9,357,776.

(30) Foreign Application Priority Data

Aug. 26, 2011 (JP) ...................... PCT/JP2011/069352
Feb. 29, 2012 (JP) ................................. 2012-043880

(51) Int. Cl.
*C07D 211/84* (2006.01)
*A01N 43/40* (2006.01)
(Continued)

(52) U.S. Cl.
CPC ............. *A01N 43/40* (2013.01); *A01N 43/54* (2013.01); *A01N 43/78* (2013.01); *C07D 211/84* (2013.01);
(Continued)

(58) Field of Classification Search
CPC .. C07D 211/84; C07D 417/06; C07D 401/06; C07D 213/75; A01N 43/40; A01N 43/78; A01N 43/54
(Continued)

(56) References Cited

U.S. PATENT DOCUMENTS 5,250,498 A 10/1993 Andree et al.
8,957,214 B2 2/2015 Kagabu et al.
(Continued)

FOREIGN PATENT DOCUMENTS

EP 0268915 6/1988
EP 0432600 6/1991
(Continued)

OTHER PUBLICATIONS

Osmialowski; J. Phys. Chem. A 2010, 114, 10421-10426.*
(Continued)

*Primary Examiner* — Daniel Carcanague
(74) *Attorney, Agent, or Firm* — Sughrue Mion, PLLC

(57) ABSTRACT

To supply a derivative having a 2-acyliminopyridine structure and being represented by the following formula (I) in an amount required as a pest control agent stably and at a low cost, provided is a method comprising the steps of: acylating an amino group at position 2 of a compound represented by formula (A) by use of an acylating agent, to thereby produce a compound represented by formula (B); and further alkylating a nitrogen atom at position 1 of the compound represented by formula (B):

(Continued)

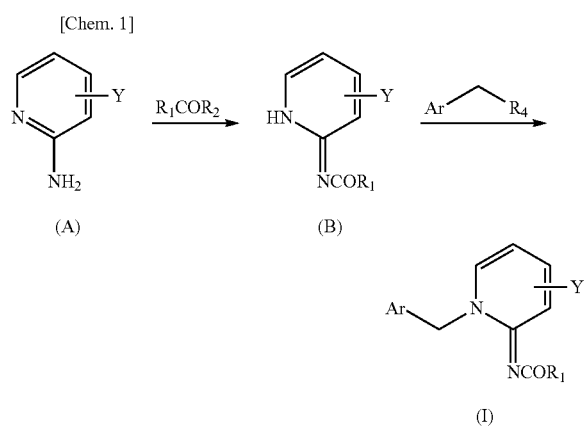

[where Ar represents a phenyl group or a 5- to 6-membered heterocycle, $R_1$ represents a $C_{1-6}$ alkyl group, and Y represents a hydrogen atom; a halogen atom; a hydroxyl group; a $C_{1-6}$ alkyl group which may be substituted with a halogen atom; a $C_{1-6}$ alkyloxy group which may be substituted with a halogen atom; a cyano group; a formyl group; or a nitro group].

9 Claims, 6 Drawing Sheets

(51) Int. Cl.
*A01N 43/78* (2006.01)
*C07D 401/06* (2006.01)
*C07D 213/75* (2006.01)
*A01N 43/54* (2006.01)
*C07D 417/06* (2006.01)

(52) U.S. Cl.
CPC ......... *C07D 213/75* (2013.01); *C07D 401/06* (2013.01); *C07D 417/06* (2013.01)

(58) Field of Classification Search
USPC .................................. 514/352; 546/265, 309
See application file for complete search history.

(56) References Cited

U.S. PATENT DOCUMENTS

| | | | |
|---|---|---|---|
| 9,073,866 B2 * | 7/2015 | Kagabu | ................ A01N 43/40 |
| 9,301,525 B2 * | 4/2016 | Horikoshi | ............ C07D 213/75 |
| 2008/0312435 A1 | 12/2008 | Saito et al. | |
| 2013/0150414 A1 | 6/2013 | Kagabu et al. | |
| 2013/0165482 A1 | 6/2013 | Kagabu et al. | |
| 2014/0315839 A1 | 10/2014 | Horikoshi et al. | |
| 2015/0005347 A1 | 1/2015 | Kagabu et al. | |
| 2015/0105427 A1 | 4/2015 | Kagabu et al. | |
| 2016/0165888 A1 * | 6/2016 | Horikoshi | ............ C07D 213/75 514/312 |
| 2017/0073312 A1 * | 3/2017 | Nakanishi | ............ C07D 213/75 |

FOREIGN PATENT DOCUMENTS

| | | |
|---|---|---|
| EP | 0639569 | 2/1995 |
| JP | 63150275 | 6/1988 |
| JP | 03190859 | 8/1991 |
| JP | 05078323 | 3/1993 |
| WO | 2006051704 | 5/2006 |
| WO | 2012029672 | 3/2012 |

OTHER PUBLICATIONS

Abarghaz et al., "Regloselective Alkylation of the Exocyclic Nitrogen of Heterocyclic Amidines via the Mitsunobu Reaction", Tetrahedron Letters, 36(36):6463-6466 (1995).
Bissell et al., "Synthesis of Three [(Trifluoroethyl)amino] pyridines", J. Chem. Eng. Data, 26(2):234-235 (1981).
Communication for European Application No. 12828367.8 dated Apr. 21, 2015.
International Preliminary Examination Report for PCT/JP2012/071399 dated Mar. 4, 2014, with Written Opinion.
International Search Report of PCT/JP2012/071399 dated Oct. 23, 2012.
Krohnke, "Imidazopyridines and related ring systems. II. Syntheses of imidazopyridines. 2", Chemische Berichte, 88:1103-1108 (1955).
Matsumura et al., "Species-specific insecticide resistance to imidacloprid and fipronil in the rice planthoppers *Nilaparvata lugens* and *Sogatella furcifera* in East and South-east Asia", Pest Management Science, 64(11):1115-1121 (2008).
Pietrzycki, "Tautomerism and rotamerism in 2- (methylamino)-, 2-anilino-, 2-acetamido-, and 2-benzamidopyridine", Bulletin des Societes Chimiques Beiges, 102(11-12):709-717 (1993).
Spencer et al., "Practical cleavage of trifluoroacetamides with p-toluensulfonic acid", Tetrahedron Letters, 50:1010-1012 (2009).
Singh, "Synthesis and Biological Evaluation of Some Pyrazolinylpyridines and Pyrazolylpyridines", Arch. Pharm. Chem. Life Sci., 339:24-31 (2006).
Dorwold, "Side Reactions in Organic Synthesis: A Guide to Successful Synthesis Design", Side Reactions in Organic Synthesis, Wiley, Preface and Chapter 1 (2005).

* cited by examiner

METHOD FOR PRODUCING PEST CONTROL AGENT

CROSS REFERENCE TO RELATED APPLICATIONS

This is a Divisional of U.S. application Ser. No. 14/238,299, filed Mar. 24, 2014 (now allowed); which is a National Stage of International Application No. PCT/JP2012/071399 filed Aug. 24, 2012; which claims priority based on International Application No. PCT/JP2011/069352 filed Aug. 26, 2011, and Japanese Patent Application No. 2012-043880 filed Feb. 29, 2012.

BACKGROUND OF THE INVENTION

Field of the Invention

The present invention relates to a method for producing a novel pest control agent having a 2-acyliminopyridine structure.

Related Background Art

Although many pest control agents have been developed so far, novel agents are still sought because of problems associated with decreased drug sensitivity, persistence of the effects of agents, safety of agents in use, and the like.

In particular, as shown in Masaya Matsumura et al., Pest Management Science, 2008, Vol. 64, No. 11, pp. 1115 to 1121 (Non-Patent Document 1), wet rice cultivation in East Asia and Southeast Asia obviously suffers damage due to planthoppers which have developed drug resistance to major pesticides including neonicotinoids represented by imidacloprid, phenylpyrazole-based agents represented by fipronil, and the like. Accordingly, specific agents against planthoppers which have developed resistance have been expected. In addition, it is required that such novel agents be provided in amounts required as pest control agents stably and at low costs.

Methods described in DESCRIPTION of European Patent Application Publication No. 432600 (Patent Document 1), Japanese Unexamined Patent Application Publication No. Hei 05-78323 (Patent Document 2), DESCRIPTION of European Patent Application Publication No. 268915 (Patent Document 3), and Botho Kickhofen et al., Chemische Berichte, 1955, Vol. 88, pp. 1103 to 1108 (Non-Patent Document 2) are known as methods for producing a pest control agent having a 2-acyliminopyridine structure. Patent Document 1 discloses a herbicide having the same ring structure as that of a compound represented by formula (I) described later. Patent Documents 2 and 3 disclose pesticides having the same ring structure as that of the compound represented by formula (I). Non-Patent Document 2 discloses a compound having a ring structure similar to that of the compound represented by formula (I), as a synthetic intermediate.

However, the production methods described in Patent Documents 1, 2, and 3, and Non-Patent Document 2 are production methods in which a compound represented by formula (Ba) described later is used as an intermediate, and fail to describe production in which a compound represented by formula (B) described later is used as an intermediate. Moreover, Patent Documents 1, 2, and 3, and Non-Patent Document 2 disclose production methods in which a compound represented by formula (Ba) is used as an intermediate, but do not specifically describe the production of a compound represented by formula (Ia) described later. Further, the structural formula of N-[1-((6-chloropyridin-3-yl)methyl)pyridin-2(1H)-ylidene]-2,2,2-trifluoroacetamide is disclosed, and a physical property value of the compound, i.e., a refractive index nD (25.5) of 1.4818 is described (Compound No. 3 in Table 1 of Patent Document 2); however, this compound is not included in the list of compounds shown to have pest control activities (Tables 2 and 3 of Patent Document 2).

Moreover, Patent Document 3 discloses the structural formula of N-[1-((6-chloropyridin-3-yl)methyl)pyridin-2(1H)-ylidene]-2,2,2-trifluoroacetamide, and describes a physical property value of the compound, i.e., a melting point of 60 to 62° C. (Example No. 12 in Table 7 of Patent Document 3). However, this compound is not listed in the examples of compounds which exhibited pest control activities in Examples. Neither Patent Document 2 nor Patent Document 3 discloses a specific method for producing N-[1-((6-chloropyridin-3-yl)methyl)pyridin-2(1H)-ylidene]-2,2,2-trifluoroacetamide.

In addition, Wladysl, aw Pietrzycki, et al., Bulletin des Societes Chimiques Belges, 1993, Vol. 102, No. 11-12, pp. 709 to 717 (Non-Patent Document 3) discloses N-(pyridin-2(1H)-ylidene]-acetamide as a tautomer of 2-acetamide pyridine, but fails to describe a specific method for producing the tautomer, or a method for producing a haloacyl derivative thereof.

SUMMARY OF THE INVENTION

Problem to be Solved by the Invention

An object of the present invention is to provide a pest control agent having a 2-acyliminopyridine structure and being represented by formula (I) described later, in particular N-[1-((6-chloropyridin-3-yl)methyl)pyridin-2(1H)-ylidene]-2,2,2-trifluoroacetamide, in an amount required for a pest control agent stably and at a low cost.

Means for Solving the Problem

Specifically, according to a first aspect of the invention, the present inventors have obtained a desired useful compound represented by the following formula (I) by using a compound represented by formula (A) as a starting substance, and a compound represented by formula (B) as an intermediate. As a result, the present invention has been completed.

Provided is a method for producing a compound represented by the following formula (I):

[Chem. 1]

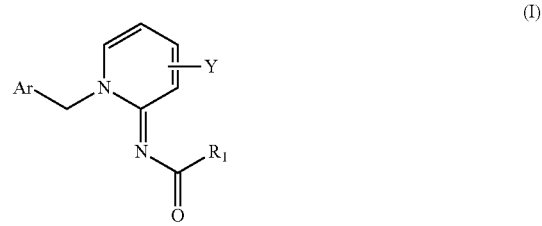

(I)

[where Ar represents a phenyl group which may be substituted or a 5- to 6-membered heterocycle which may be substituted, $R_1$ represents a $C_{1-6}$ alkyl group which may be substituted, and Y represents a hydrogen atom; a halogen atom; a hydroxyl group; a $C_{1-6}$ alkyl group which may be substituted with a halogen atom; a $C_{1-6}$ alkyloxy group which may be substituted with a halogen atom; a cyano group; a formyl group; or a nitro group], the method comprising, as shown in the following reaction formula:

[Chem. 2]

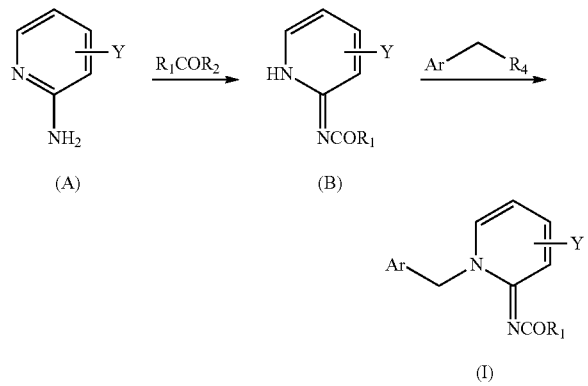

(I)

[where $R_1$ and Y have the same meanings as those described above, $R_2$ represents (1) a trifluoroacetoxy group, (2) a $C_{1-6}$ alkyloxy group which may be substituted with a halogen atom or a benzyloxy group whose phenyl group may be substituted with a halogen atom, a methyl group, a cyano group, a nitro group, or a methoxy group, (3) a $C_{1-6}$ alkylcarbonyloxy group which may be substituted with a halogen atom (provided that a trifluoroacetoxy group is excluded) or a phenylcarbonyloxy group whose phenyl group may be substituted with a halogen atom, a methyl group, a cyano group, a nitro group, or a methoxy group, (4) a hydroxyl group, or (5) a halogen atom, and $R_4$ represents a halogen atom, a $C_{1-6}$ alkylsulfoxy group which may be substituted with a halogen atom, or a phenylsulfoxy group which may be substituted with a halogen atom or a methyl group], the steps of:

acylating an amino group at position 2 of a compound represented by formula (A) by use of an acylating agent represented by $R_1COR_2$, to thereby produce a compound represented by formula (B);

[Chem. 3]

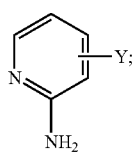

(A)

and further alkylating a nitrogen atom at position 1 of the compound represented by formula (B) by use of Ar—$CH_2$—$R_4$.

A second aspect of the present invention provides a useful intermediate represented by formula (B) (provided that compounds in which $R_1$ is a methyl group or a phenyl group, and Y is a hydrogen atom are excluded), and a salt thereof.

A third aspect of the present invention provides a method for producing a compound represented by the following formula (Ia):

[Chem. 4]

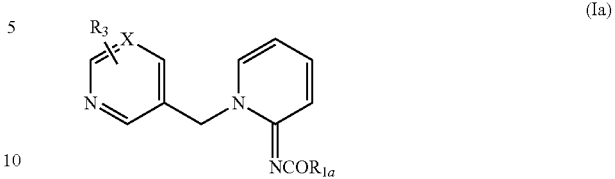

[where $R_3$ represents a halogen atom, a cyano group, a nitro group, or a trifluoromethyl group, X represents a carbon atom or a nitrogen atom, and $R_{1a}$ represents a halogen-substituted $C_{1-6}$ alkyl group], the method being shown by the following reaction formula:

[Chem. 5]

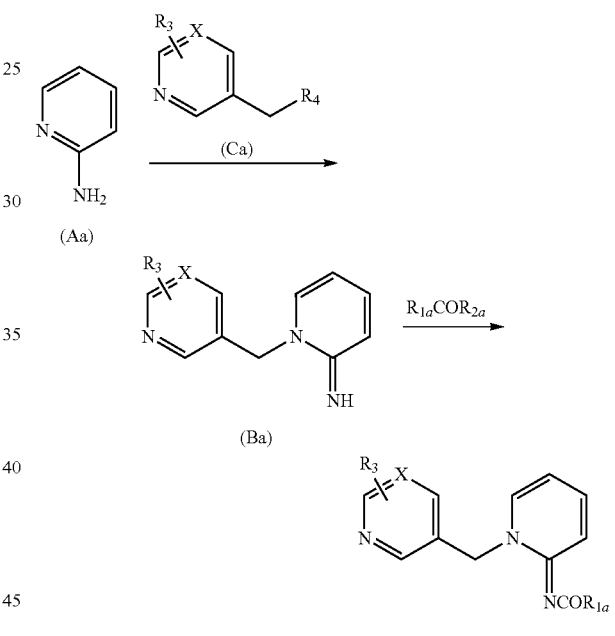

[where $R_{1a}$, $R_4$, $R_3$ and X have the same meanings as those described above, $R_{2a}$ represents (1) a trifluoroacetoxy group, (2) a $C_{1-6}$ alkyloxy group which may be substituted with a halogen atom or a benzyloxy group whose phenyl group may be substituted with a halogen atom, a methyl group, a cyano group, a nitro group, or a methoxy group, (3) a $C_{1-6}$ alkylcarbonyloxy group which may be substituted with a halogen atom (provided that a trifluoroacetoxy group is excluded) or a phenylcarbonyloxy group whose phenyl group may be substituted with a halogen atom, a methyl group, a cyano group, a nitro group, or a methoxy group, (4) a hydroxyl group, or (5) a halogen atom].

A fourth aspect of the present invention provides a compound represented by formula (I'), which is produced according to the following reaction formula:

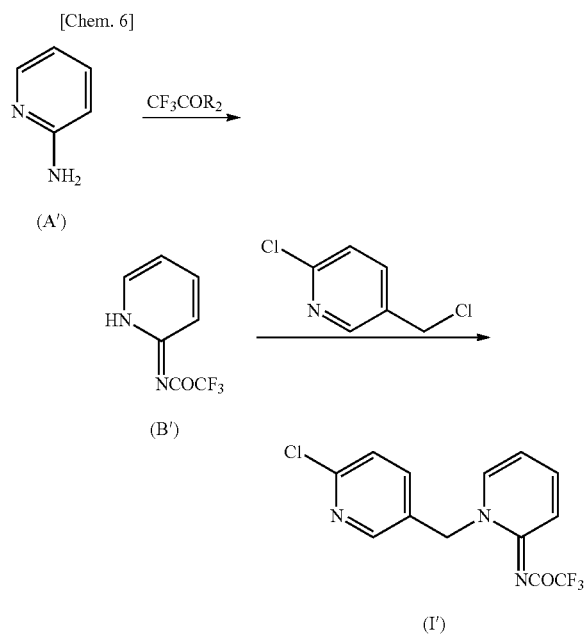

[where the compound represented by formula (I') is N-[1-((6-chloropyridin-3-yl)methyl)pyridin-2(1H)-ylidene]-2,2,2-trifluoroacetamide which has the following physical properties (a) and/or (b):

(a) diffraction angle peaks determined by powder X-ray diffraction being present at least at the following diffraction angles (2θ): 8.6±0.2°, 14.2±0.2°, 17.5±0.2°, 18.3±0.2°, 19.7±0.2°, 22.3±0.2°, 30.9±0.2°, and 35.3±0.2°;

(b) a melting point determined by differential scanning calorimetry (DSC) of 155 to 158° C.]

Effects of the Invention

According to the present invention, a 2-acyliminopyridine derivative useful as a pest control agent can be produced efficiently in a good yield and, if necessary, in a one-pot manner.

DETAILED DESCRIPTION OF THE PREFERRED EMBODIMENTS

Figure 1:
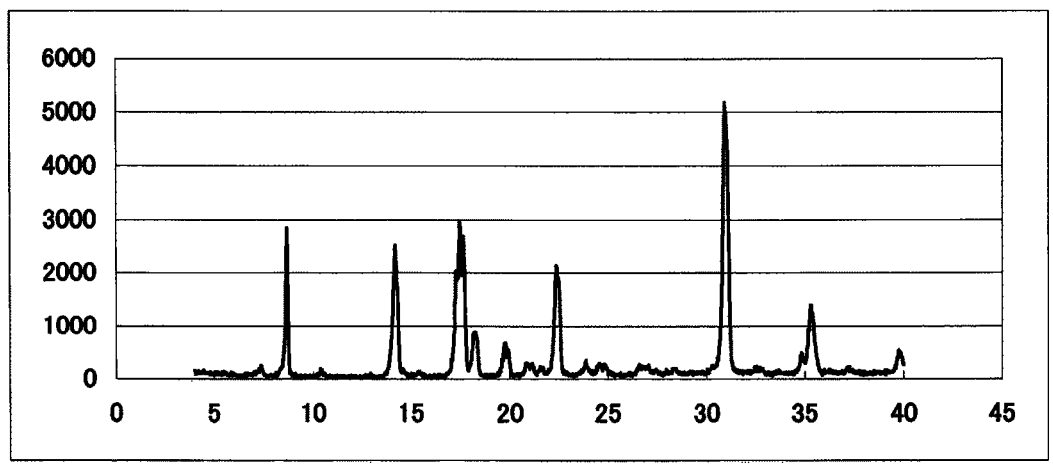
FIG. 1 is a graph showing results of powder X-ray crystallography conducted on crystals of N-[1-((6-chloropyridin-3-yl)methyl)pyridin-2(1H)-ylidene]-2,2,2-trifluoroacetamide prepared by a first production method.

The "alkyl" used herein either as a substituent or a portion of a substituent means a linear, branched, or cyclic alkyl, or an alkyl of a combination of any of these, unless otherwise defined.

The "halogen atom" used herein means an atom selected from fluorine, chlorine, bromine, and iodine.

The term "equivalent" of the base used herein is, for example, as follows: when 1 mol of potassium carbonate is used for 1 mol of a compound represented by formula (A), the potassium carbonate is 2 equivalents; when 1 mol of sodium hydroxide or sodium hydrogen carbonate is used therefor, the sodium hydroxide or sodium hydrogen carbonate is 1 equivalent; and when 1 mol of an organic base is used therefor, the organic base is 1 equivalent.

The "salt" used herein refers to an inorganic acid salt such as a hydrochloride, a sulfuric acid salt, or a nitric acid salt; an organic acid salt such as a trifluoroacetic acid salt, a difluoroacetic acid salt, a dichloroacetic acid salt; or the like.

The "reagent used simultaneously with an acylating agent $R_1COR_2$" used herein may be a hydrate thereof, when $R_2$ represents a hydroxyl group.

The "condensation agent" used herein is a reagent for synthesis of carboxylic acid derivatives such as esters and amides, and examples of the "condensation agent" includes N,N'-dicyclohexylcarbodiimide, 1-ethyl-3-(3-dimethylaminopropyl)carbodiimide hydrochloride, 1,1'-carbonyldiimidazole, dipyridyl disulfide, diimidazolyl disulfide, 1,3,5-trichlorobenzoyl chloride, 1,3,5-trichlorobenzoyl anhydride, PyBop (registered trademark, (benzotriazole-1-yloxy)tripyrrolidinophosphonium hexafluorophosphate), and PyBrop (registered trademark, bromotri(pyrrolidino)phosphonium hexafluorophosphate), and the like.

The sign "$C_{a-b}$" used herein and attached to a substituent means that the number of carbon atoms contained in the substituent is in the range from a to b. Moreover, for example, the "$C_{a-b}$" in a case of "$C_{a-b}$ alkylcarbonyloxy" means that the number of carbon atoms in the alkyl moiety excluding the carbon atom in the carbonyloxy moiety is in the range from a to b.

Ar represents a phenyl group which may be substituted or a 5- to 6-membered heterocycle which may be substituted. Examples of the 5- to 6-membered heterocycle include pyridine, pyrimidine, thiazole, tetrahydrofuran, furan, and the like. Preferred examples of Ar include a 3-pyridyl group, a 5-pyrimidyl group, a 3-thiazolyl group, a 5-thiazolyl group, and a 3-pyridyl group is more preferable. Examples of a substituent which may be introduced to the phenyl group or the heterocycle include halogen atoms, $C_{1-4}$ alkyl groups which may be substituted with a halogen atom, $C_{1-4}$ alkyloxy groups which may be substituted with a halogen atom, a hydroxyl group, a cyano group, and a nitro group. Here, halogen atoms and $C_{1-4}$ alkyl groups which may be substituted with a halogen atom are preferable, and a chlorine atom is particularly preferable. Specific examples of the phenyl group which may be substituted and the 5- to 6-membered heterocycle which may be substituted include a phenyl group, a 3-chlorophenyl group, a 4-chlorophenyl group, a 3-cyanophenyl group, a 4-cyanophenyl group, a 3-nitrophenyl group, a 4-nitrophenyl group, a 3,5-dichlorophenyl group, a 4-methylphenyl group, a 4-methoxyphenyl group, a 3,5-dibromophenyl group, a 2,4-dibromophenyl group, a 4-fluorophenyl group, a 4-bromophenyl group, a 3-nitro-5-bromophenyl group, a 3,5-bis(trifluoromethyl)phenyl group, a 6-chloro-3-pyridyl group, a 2-chloro-5-thiazolyl group, a 6-chloro-5-fluoro-3-pyridyl group, a 6-bromo-3-pyridyl group, a 6-fluoro-3-pyridyl group, a 5,6-dichloro-3-pyridyl group, and a 6-trifluoromethyl-3-pyridyl group. Here, a 6-chloro-3-pyridyl group, a 6-fluoro-3-pyridyl group, a 6-chloro-5-fluoro-3-pyridyl group, and a 6-bromo-3-pyridyl group are preferable, and a 6-chloro-3-pyridyl group is particularly preferable.

$R_1$ represents a $C_{1-6}$ alkyl group which may be substituted. Examples of a substituent which may be introduced to the $C_{1-6}$ alkyl group include halogen atoms, $C_{1-6}$ halogenated alkyloxy groups, a cyano group, a nitro group, and a hydroxyl group. Specific examples of the $C_{1-6}$ alkyl group represented by $R_1$ include a trifluoromethyl group, a difluorochloromethyl group, a trichloromethyl group, a pentafluoroethyl group, a difluoromethyl group, a dichloromethyl group, a dibromomethyl group, a chloromethyl group, a difluoroethyl group, a dichloroethyl group, a 2,2,2-trifluoroethyl group, a difluorocyclopropyl group, a bromodifluoromethyl group, a trifluoromethoxymethyl group, and the like; preferred examples thereof include a trifluoromethyl group, a difluorochloromethyl group, a difluoromethyl group, a trichloromethyl group, and a pentafluoroethyl group; and a more preferred example is a trifluoromethyl group.

$R_{1a}$ represents a halogen-substituted $C_{1-6}$ alkyl group. Examples thereof include a trifluoromethyl group, a trichloromethyl group, a difluorochloromethyl group, a difluoromethyl group, a dichloromethyl group, a dibromomethyl group, a chloromethyl group, a difluoroethyl group, a dichloroethyl group, a 2,2,2-trifluoroethyl group, a pentafluoroethyl group, a difluorocyclopropyl group, and the like. Here, a trifluoromethyl group, a trichloromethyl group, a dichloromethyl group, a difluoromethyl group, a difluorochloromethyl group, a chloromethyl group, and a pentafluoroethyl group are preferable; a trifluoromethyl group, a difluoromethyl group, a difluorochloromethyl group, a chloromethyl group, and a pentafluoroethyl group are more preferable; and a trifluoromethyl group is particularly preferable.

Y represents a hydrogen atom; a halogen atom; a hydroxyl group; a $C_{1-6}$ alkyl group which may be substituted with a halogen atom; a $C_{1-6}$ alkyloxy group which may be substituted with a halogen atom; a cyano group; a formyl group; or a nitro group. Y preferably represents a hydrogen atom, a halogen atom, or a hydroxyl group, and more preferably represents a hydrogen atom.

Each of $R_2$ and $R_{2a}$ represents (1) a trifluoroacetoxy group, (2) a $C_{1-6}$ alkyloxy group which may be substituted with a halogen atom or a benzyloxy group whose phenyl group may be substituted with a halogen atom, a methyl group, a cyano group, a nitro group, or a methoxy group, (3) a $C_{1-6}$ alkylcarbonyloxy group which may be substituted with a halogen atom (provided that a trifluoroacetoxy group is excluded) or a phenylcarbonyloxy group whose phenyl group may be substituted with a halogen atom, a methyl group, a cyano group, a nitro group, or a methoxy group, (4) a hydroxyl group, or (5) a halogen atom.

$R_3$ represents a substituent substituted on a carbon atom of a pyridine ring or a pyrimidine ring, and it is evident that the number of $R_3$ is 0 to 4 in the case of pyridine, and 0 to 3 in the case of the pyrimidine ring. Each of the substituents represented by $R_3$ is a halogen atom, a cyano group, a nitro group, or a trifluoromethyl group, and the substituents may be the same or different.

$R_4$ represents a halogen, a $C_{1-6}$ alkylsulfoxy group which may be substituted with a halogen atom, or a phenylsulfoxy group which may be substituted with a halogen atom or a methyl group.

Preferred examples of the compound represented by formula (I) or (Ia) include Compound No. 1: N-[1-((6-chloropyridin-3-yl)methyl)pyridin-2(1H)-ylidene]-2,2,2-trifluoroacetamide, Compound No. 2: N-[1-((6-chloro-5-fluoropyridin-3-yl)methyl)pyridin-2(1H)-ylidene]-2,2,2-trifluoroacetamide, Compound No. 19: N-[1-((6-fluoropyridin-3-yl)methyl)pyridin-2(1H)-ylidene]-2,2,2-trifluoroacetamide, Compound No. 3: N-[1-((6-bromopyridin-3-yl)methyl)pyridin-2(1H)-ylidene]-2,2,2-trifluoroacetamide, Compound No. 8: N-[1-((6-chloropyridin-3-yl)methyl)pyridin-2(1H)-ylidene]-2,2-difluoroacetamide, Compound No. 4: 2-chloro-N-[1-((6-chloropyridin-3-yl)methyl)pyridin-2(1H)-ylidene]-2,2-difluoroacetamide, Compound No. 7: N-[1-((6-chloropyridin-3-yl)methyl)pyridin-2(1H)-ylidene]-2,2,3,3,3-pentafluoropropanamide, and Compound No. 6: N-[1-((2-chloropyrimidin-5-yl)methyl)pyridin-2(1H)-ylidene]-2,2,2-trifluoroacetamide.

Of these compounds represented by formula (I) or formula (Ia), a particularly preferred example is a compound represented by formula (I'), i.e., N-[1-((6-chloropyridin-3-yl)methyl)pyridin-2(1H)-ylidene]-2,2,2-trifluoroacetamide which has the following physical properties (a) and/or (b) (provided that the compound with nD(25.5)=1.4818 described in Patent Document 2 is excluded):

(a) diffraction angle peaks determined by powder X-ray diffraction being present at least at the following diffraction angles (2θ): 8.6±0.2°, 14.2±0.2°, 17.5±0.2°, 18.3±0.2°, 19.7±0.2°, 22.3±0.2°, 30.9±0.2°, and 35.3±0.2°;

(b) a melting point determined by differential scanning calorimetry (DSC) of 155 to 158° C.

Preferred examples of the compound represented by formula (B) include 2,2,2-trifluoro-N-(pyridin-2(1H)-ylidene)acetamide, 2-chloro-2,2-difluoro-N-(pyridin-2(1H)-ylidene)acetamide, 2,2,3,3,3-pentafluoro-N-(pyridin-2(1H)-ylidene)propan amide, and 2,2-difluoro-N-(pyridin-2(1H)-ylidene)acetamide; and a more preferred example is 2,2,2-trifluoro-N-(pyridin-2(1H)-ylidene)acetamide represented by the following formula (B1):

[Chem. 7]

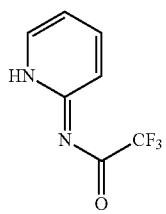

(B1)

Production Method

The present invention will be described in further detail according to the following scheme.

[Chem. 8]

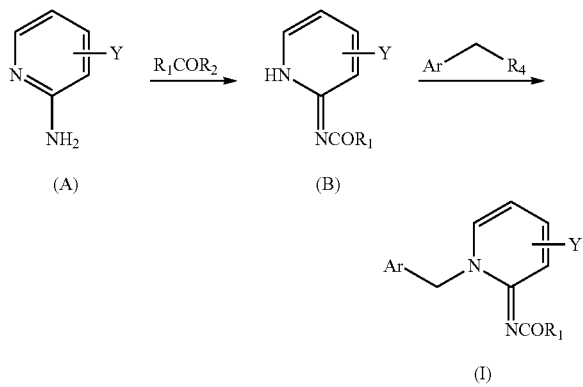

[in the above scheme, Ar, Y, $R_1$, $R_2$, and $R_4$ have the same meanings as those described above].

In addition, the compound represented by formula (B) shown in the above scheme may be used for the subsequent step, without post treatment or isolation.

1-1: Production of Compound Represented by Formula (B) from Compound Represented by Formula (A)

The compound represented by formula (A) can be obtained as a commercially available compound, or can be obtained by the method described in Journal of labeled compounds & radiopharmaceuticals (1987), 24(2), 119-123, for example.

A method for producing a compound represented by formula (B) from a compound represented by formula (A) is as follows. Specifically, the compound represented by formula (B) can be obtained by reacting the compound represented by formula (A) with an acylating agent $R_1COR_2$ ($R_1$ and $R_2$ have the same meanings as those defined above) without a solvent or in a solvent which does not affect the reaction in the presence of or in the absence of a base.

Here, the numbers of equivalents of reagents are all the numbers of equivalents to the compound represented by formula (A).

Examples of usable solvents include aromatic hydrocarbon-based solvents such as toluene, xylene, and ethylbenzene; ester-based solvents such as ethyl acetate and butyl acetate; ether-based solvents such as diethyl ether, diisopropyl ether, tetrahydrofuran, and dioxane; aprotic polar organic solvents such as N,N-dimethylformamide, dimethyl sulfoxide, N,N-dimethylacetamide, N-methyl-2-pyrrolidinone, and acetonitrile; halogen-containing solvents such as dichloromethane and chloroform; hydrocarbon-based solvent such as cyclohexane; ketone-based solvents such as acetone and methyl ethyl ketone; water; and mixture solvents thereof.

Examples of usable bases include inorganic bases such as sodium carbonate, potassium carbonate, sodium hydrogen carbonate, potassium hydrogen carbonate, sodium hydroxide, magnesium hydroxide, calcium hydroxide, lithium hydroxide, and barium hydroxide; organic bases such as 1,8-diazabicyclo[5.4.0]undec-7-ene, 1,5-diazabicyclo[4.3.0] non-5-ene, triethylamine, diisopropylethylamine, pyridine, picoline, and dimethylaminopyridine; and alcoholates such as sodium ethoxide, sodium methoxide, and potassium tert-butoxide. The base does not necessarily need to be used; however, when the reaction is carried out in the presence of a base, the base can be used in an amount of 0.01 to 20.0 equivalents.

Examples of the acylating agent $R_1COR_2$ include trifluoroacetic anhydride, trifluoroacetic acid, ethyl trifluoroacetate, trifluoroacetyl chloride, and mixed acid anhydrides. In addition, these acylating agents may be used alone or in combination of two or more. Of these acylating agents, trifluoroacetic anhydride, trifluoroacetic acid, ethyl trifluoroacetate, or trifluoroacetyl chloride can be preferably used. In addition, when $R_2$ represents a hydroxyl group, the reaction can be carried out by simultaneously using a condensation agent such as N,N'-dicyclohexylcarbodiimide, 1-ethyl-3-(3-dimethylaminopropyl)carbodiimide hydrochloride, 1,1'-carbonyldiimidazole, dipyridyl disulfide, diimidazolyl disulfide, 1,3,5-trichlorobenzoyl chloride, 1,3,5-trichlorobenzoyl anhydride, PyBop (registered trademark, (benzotriazole-1-yloxy)tripyrrolidinophosphonium hexafluorophosphate), or PyBrop (registered trademark, bromotri(pyrrolidino) phosphonium hexafluorophosphate); or a reagent such as phosphorus pentoxide, sulfuric acid, polyphosphoric acid, thionyl chloride, phosphorus oxychloride, oxalyl dichloride, boron trifluoride, p-toluenesulfonic acid, or a halide, a sulfate, a nitrate, or an oxide of iron, cobalt, copper, nickel, zinc, aluminum, lithium, or magnesium. In addition, these reagents may be used alone or in combination of two or more. Preferred examples of the halide, the sulfate, the nitrate, or the oxide of iron, cobalt, copper, nickel, zinc, aluminum, lithium, or magnesium include zinc chloride, copper chloride, magnesium chloride, cobalt chloride, nickel chloride, ferric chloride, aluminum chloride, ferric sulfate, and aluminum sulfate. These compounds of metals may be anhydrides or hydrates thereof. The amount of the acylating agent used is preferably 0.5 to 10.0 equivalents, and more preferably 1.0 to 5.0 equivalents.

The reaction temperature is preferably in a range from −80° C. to 200° C. The reaction time is preferably in a range from 0.1 hours to 7 days.

Preferred modes are as follows:

(1) When $R_2$ represents a trifluoroacetoxy group, specifically, when trifluoroacetic anhydride is used as the acylating agent, examples of preferred solvents include ester-based solvents such as ethyl acetate and butyl acetate; halogen-containing solvents such as dichloromethane and chloroform; and aromatic hydrocarbon-based solvents such as toluene, xylene, and ethylbenzene. Here, toluene is more preferable. The reaction is preferably carried out in the absence of a base; however, when a base is used, preferred examples of the base include sodium carbonate, potassium carbonate, potassium hydrogen carbonate, triethylamine, pyridine, and the like. Here, potassium carbonate is more preferable. The amount of the acylating agent used is preferably 1.0 to 5.0 equivalents, and more preferably 1.0 to 1.5 equivalents. When the base is used, the amount of the base used is preferably 1.0 to 4.5 equivalents, and more preferably 1.0 to 3.0 equivalents. The reaction temperature is preferably in a range from −20° C. to 50° C., and more preferably from −10° C. to 30° C. The reaction time is preferably in a range from 0.1 hours to 7 days, and more preferably in a range from 0.5 hours to 4 hours. Particularly preferred conditions are as follows: trifluoroacetic anhydride is used as the acylating agent; toluene is used as the solvent; the amount of the acylating agent used is 1.0 to 1.5 equivalents; the reaction temperature is −10° C. to 30° C.; and the reaction time is 0.5 to 4 hours. Regarding the base, no base is used, or when a base is used, potassium carbonate is used in an amount of 1.0 to 3.0 equivalents.

(2) When $R_2$ represents a $C_{1-6}$ alkyloxy group which may be substituted with a halogen atom or a benzyloxy group whose phenyl group may be substituted with a halogen atom, a methyl group, a cyano group, a nitro group, or a methoxy group, specifically when ethyl trifluoroacetate, methyl trifluoroacetate, or propyl trifluoroacetate is used, particularly preferably when ethyl trifluoroacetate or the like is used, preferred examples of the solvent include aprotic polar organic solvents such as N,N-dimethylformamide, dimethyl sulfoxide, N,N-dimethylacetamide, N-methyl-2-pyrrolidinone, and acetonitrile; ether-based solvents such as diethyl ether, diisopropyl ether, tetrahydrofuran, and dioxane; and mixture solvents of any of these solvents with an aromatic hydrocarbon-based solvent such as toluene, xylene, or ethylbenzene. Here, N,N-dimethylformamide or a mixture solvent of N,N-dimethylformamide with toluene is more preferable. The reaction is preferably carried out in the absence of a base; however, when a base is used, preferred examples of the base include potassium carbonate, triethylamine, dimethylaminopyridine, and the like. Here, potassium carbonate and dimethylaminopyridine are more preferable. The amount of the acylating agent used is preferably 1.0 to 5.0 equivalents, and more preferably 1.5 to 5.0 equivalents. When the base is used, the amount of the base used is preferably 0.01 to 3.0 equivalents, and more preferably 0.01 to 2.0 equivalents. The reaction temperature is preferably in a range from 20° C. to 100° C., and more preferably from 40° C. to 80° C. The reaction time is preferably in a range from 0.1 hours to 7 days, and more preferably in a range from 1 hour to 2 days.

Particularly preferred conditions are as follows: ethyl trifluoroacetate is used as the acylating agent; N,N-dimethylformamide or a mixture solvent of N,N-dimethylformamide with toluene is used as the solvent; the amount of the acylating agent used is 1.5 to 5.0 equivalents; the reaction temperature is 40° C. to 80° C.; and the reaction time is 2 hours to 2 days. Regarding the base, no base is used, or when a base is used, potassium carbonate or dimethylaminopyridine is used in an amount of 0.01 to 2.0 equivalents.

(3) When $R_2$ represents a $C_{1-6}$ alkylcarbonyloxy group which may be substituted with a halogen atom (provided that a trifluoroacetoxy group is excluded) or a phenylcarbonyloxy group whose phenyl group may be substituted with a halogen atom, a methyl group, a cyano group, a nitro group, or a methoxy group, a specific example is a pivaloyl group. The reaction temperature is preferably in a range from −20° C. to 50° C., and more preferably from −10° C. to 30° C. The reaction time is preferably in a range from 0.1 hours to 7 days, and more preferably in a range from 0.5 hours to 4 hours.

(4) When $R_2$ represents a hydroxyl group, specific examples of the acylating agent include trifluoroacetic acid, difluorochloroacetic acid, trichloroacetic acid, difluoroacetic acid, dichloroacetic acid, dibromoacetic acid, chloroacetic acid, difluoropropionic acid, dichloropropionic acid, 2,2,2-trifluoropropionic acid, pentafluoropropionic acid, difluorocyclopropanecarboxylic acid, and the like. Here, trifluoroacetic acid, trichloroacetic acid, dichloroacetic acid, difluoroacetic acid, difluorochloroacetic acid, chloroacetic acid, and pentafluoropropionic acid are preferable; trifluoroacetic acid, difluoroacetic acid, difluorochloroacetic acid, and pentafluoropropionic acid are more preferable; and trifluoroacetic acid is particularly preferable. When trifluoroacetic acid is used, preferred examples of the solvent include aromatic hydrocarbon-based solvents such as toluene, xylene, and ethylbenzene; and aprotic polar organic solvents such as N,N-dimethylformamide, dimethyl sulfoxide, N,N-dimethylacetamide, N-methyl-2-pyrrolidinone, and acetonitrile. Here, toluene, xylene, N,N-dimethylformamide, N-methyl-2-pyrrolidinone, N,N-dimethylacetamide, a mixture solvent of toluene with N,N-dimethylformamide, a mixture solvent of xylene with N,N-dimethylformamide, a mixture solvent of xylene with N-methyl-2-pyrrolidinone, or a mixture solvent of xylene with N,N-dimethylacetamide is more preferable. Examples of the reagent used simultaneously include N,N'-dicyclohexylcarbodiimide, 1-ethyl-3-(3-dimethylaminopropyl)carbodiimide hydrochloride, phosphorus pentoxide, sulfuric acid, polyphosphoric acid, thionyl chloride, phosphorus oxychloride, oxalyl dichloride, and the like. The reagent is preferably used in an amount of 0.2 to 5.0 equivalents. In addition, when zinc chloride, copper chloride, magnesium chloride, cobalt chloride, nickel chloride, ferric chloride, aluminum chloride, ferric sulfate, aluminum sulfate, boron trifluoride, p-toluenesulfonic acid, or the like is used as the reagent used simultaneously, the reagent is preferably used in an amount of 0.0001 to 1.0 equivalents. The reaction is preferably carried out in the absence of a base, when phosphorus pentoxide, sulfuric acid, polyphosphoric acid, thionyl chloride, phosphorus oxychloride, oxalyl dichloride, zinc chloride, copper chloride, magnesium chloride, cobalt chloride, nickel chloride, ferric chloride, aluminum chloride, ferric sulfate, aluminum sulfate, boron trifluoride, or p-toluenesulfonic acid is used. Meanwhile, the reaction is preferably carried out in the presence of a base, when N,N'-dicyclohexylcarbodiimide or 1-ethyl-3-(3-dimethylaminopropyl)carbodiimide hydrochloride is used. When a base is used, preferred examples of the base include sodium carbonate, potassium carbonate, potassium hydrogen carbonate, triethylamine, pyridine, dimethylaminopyridine, and the like. Here, triethylamine is more preferable. The amount of the acylating agent used is preferably 1.0 to 5.0 equivalents, and more preferably 1.0 to 3.0 equivalents. When thionyl chloride, phosphorus oxychloride, or oxalyl dichloride is used, the reagent is preferably used in an amount of 0.2 to 5.0 equivalents, and the reaction temperature is preferably in a range from −30° C. to 80° C., and more preferably from −10° C. to 40° C. When phosphorus pentoxide, sulfuric acid, or polyphosphoric acid is used, the reagent is preferably used in an amount of 0.2 to 5.0 equivalents, and the reaction temperature is preferably in a range from −30° C. to 200° C., and more preferably from −10° C. to 160° C. When N,N'-dicyclohexylcarbodiimide or 1-ethyl-3-(3-dimethylaminopropyl)carbodiimide hydrochloride is used, the following conditions are preferable: the reagent is used in an amount of 0.2 to 5.0 equivalents; the reaction temperature is preferably in a range from −30° C. to 80° C., and more preferably from −10° C. to 40° C.; and triethylamine is used as the base in an amount of 0.2 to 5.0 equivalents. When zinc chloride, copper chloride, magnesium chloride, cobalt chloride, nickel chloride, ferric chloride, aluminum chloride, ferric sulfate, aluminum sulfate, boron trifluoride, or p-toluenesulfonic acid is used, the following conditions are preferable: the reagent is used in an amount of 0.0001 to 1.0 equivalents; the reaction temperature is preferably in a range from 20° C. to 200° C., and more preferably from 80° C. to 160° C. The reaction time is preferably in a range from 0.1 hours to 7 days, and more preferably in a range from 0.5 hours to 2 days.

Particularly preferred conditions are as follows: trifluoroacetic acid is used as the acylating agent; toluene, N,N-dimethylformamide, xylene, N-methyl-2-pyrrolidinone, N,N-dimethylacetamide, a mixture solvent of N,N-dimethylformamide with toluene, a mixture solvent of xylene with N,N-dimethylformamide, a mixture solvent of xylene with N-methyl-2-pyrrolidinone, or a mixture solvent of xylene with N,N-dimethylacetamide is used as the solvent; and the amount of the acylating agent used is 1.0 to 3.0 equivalents. When thionyl chloride, phosphorus oxychloride, or oxalyl dichloride is used, particularly preferred conditions are as follows: the reagent is used in an amount of 0.3 to 3.0 equivalents; no base is used; the reaction temperature is −10° C. to 40° C.; and the reaction time is 0.5 hours to 1 day. When phosphorus pentoxide, sulfuric acid, or polyphosphoric acid is used, particularly preferred conditions are as follows: the reagent is used in an amount of 0.2 to 2.0 equivalents; the reaction temperature is −10° C. to 160° C.; and the reaction time is 0.5 hours to 1 day. When N,N'-dicyclohexylcarbodiimide or 1-ethyl-3-(3-dimethylaminopropyl)carbodiimide hydrochloride is used, particularly preferred conditions are as follows: the reagent is used in an amount of 0.5 to 3 equivalents; the reaction temperature is −10° C. to 40° C.; triethylamine is used as the base in an amount of 0.5 to 3.0 equivalents; and the reaction time is 0.5 to 1 day. When zinc chloride, copper chloride, magnesium chloride, cobalt chloride, nickel chloride, ferric chloride, aluminum chloride, ferric sulfate, aluminum sulfate, boron trifluoride, or p-toluenesulfonic acid is used, particularly preferred conditions are as follows: the reagent is used in an amount of 0.0001 to 0.5 equivalents; no base is used; the reaction temperature is 80° C. to 160° C.; and the reaction time is 2 hours to 2 days.

(5) When $R_2$ represents a halogen atom, specifically when trifluoroacetyl chloride or trifluoroacetyl bromide is used, preferably when trifluoroacetyl chloride is used, preferred examples of the solvent include halogen-containing solvents such as chloroform and dichloromethane; aromatic hydrocarbon-based solvents such as toluene, xylene, and ethylbenzene; and aprotic polar organic solvents such as N,N-dimethylformamide, dimethyl sulfoxide, N,N-dimethylacetamide, N-methyl-2-pyrrolidinone, and acetonitrile. Here, toluene, N,N-dimethylformamide, N-methyl-2-pyrrolidinone, or a mixture solvent of any of these is more preferable. The reaction is preferably carried out in the absence of a base; however, when a base is used, preferred examples of the base include sodium carbonate, potassium carbonate, potassium hydrogen carbonate, triethylamine, pyridine, and the like. Here, potassium carbonate is more preferable. The amount of the acylating agent used is preferably 1.0 to 5.0 equivalents, and more preferably 1.0 to 3.0 equivalents. When the base is used, the amount of the base used is preferably 1.0 to 5.0 equivalents, and more preferably 1.0 to 3.0 equivalents. The reaction temperature is preferably in a range from −80° C. to 40° C., and more preferably from −30° C. to 30° C. The reaction time is preferably in a range from 0.1 hours to 7 days, and more preferably in a range from 0.5 hours to 8 hours. Meanwhile, when $R_2$ represents a chlorine atom, it is also possible to use $R_1COCl$ generated in advance by simultaneously using trifluoroacetic acid with thionyl chloride, phosphorus oxychloride, oxalic acid dichloride, or the like outside the reaction system in which the reaction of the compound represented by formula (A) is carried out.

Particularly preferred conditions are as follows: trifluoroacetyl chloride is used as the acylating agent; toluene, N,N-dimethylformamide, N-methyl-2-pyrrolidinone, or a mixture solvent of any of these is used as the solvent; the amount of the acylating agent used is 1.0 to 3.0 equivalents; the reaction temperature is −30° C. to 30° C.; and the reaction time is 0.5 hours to 8 hours. Regarding the base, particularly preferred conditions are as follows: no base is used; or when a base is used, potassium carbonate is used in an amount of 1.0 to 3.0 equivalents.

After the compound represented by formula (B) is synthesized from the compound represented by formula (A), the compound represented by formula (B) may be neutralized by use of a base. Examples of usable bases include inorganic bases such as sodium carbonate, potassium carbonate, sodium hydrogen carbonate, potassium hydrogen carbonate, sodium hydroxide, magnesium hydroxide, calcium hydroxide, lithium hydroxide, and barium hydroxide; organic bases such as 1,8-diazabicyclo[5.4.0]undec-7-ene, 1,5-diazabicyclo[4.3.0]non-5-ene, triethylamine, diisopropylethylamine, pyridine, picoline, and dimethylaminopyridine; and alcoholates such as sodium ethoxide, sodium methoxide, and potassium tert-butoxide. Here, potassium carbonate, sodium ethoxide, or triethylamine is preferable.

1-2: Production of Compound Represented by Formula (I) or Formula (I') from Compound Represented by Formula (B) or Formula (B')

A method for producing a compound represented by formula (I) or formula (I') from a compound represented by formula (B) or formula (B') is as follows. Specifically, the compound represented by formula (I) or formula (I') can be obtained by reacting the compound represented by formula (B) or formula (B') with $Ar-CH_2-R_4$ (Ar and $R_4$ have the same meanings as those defined above) without a solvent or in a solvent which does not affect the reaction in the presence of a base.

Examples of usable solvents include ether-based solvents such as diethyl ether, diisopropyl ether, tetrahydrofuran, and dioxane; aprotic polar organic solvents such as N,N-dimethylformamide, dimethyl sulfoxide, N,N-dimethylacetamide, acetonitrile, N-methyl-2-pyrrolidinone, N-methyl-2-piperazinone, N,N-dimethyl-2-imidazolidinone, and acetonitrile; halogen-containing solvents such as dichloromethane and chloroform; aromatic hydrocarbon-based solvents such as toluene, xylene, and ethylbenzene; and mixture solvents thereof; and preferred examples thereof include aprotic polar organic solvents. Here, N,N-dimethylformamide, N,N-dimethylacetamide, N-methyl-2-pyrrolidinone, N,N-dimethyl-2-imidazolidinone, acetonitrile, or a mixture solvent of N,N-dimethylformamide, N,N-dimethylacetamide, N-methyl-2-pyrrolidinone, N,N-dimethyl-2-imidazolidinone, or acetonitrile with an aromatic hydrocarbon-based solvent is more preferable; and N,N-dimethylformamide or a mixture solvent of N,N-dimethylformamide with toluene is particularly preferable.

When the reaction is carried out in the presence of a base, examples of usable bases include inorganic bases such as sodium carbonate, potassium carbonate, sodium hydrogen carbonate, potassium hydrogen carbonate, sodium hydroxide, magnesium hydroxide, calcium hydroxide, lithium hydroxide, and barium hydroxide; and organic bases such as 1,8-diazabicyclo[5.4.0]undec-7-ene, 1,5-diazabicyclo[4.3.0]non-5-ene, triethylamine, diisopropylethylamine, pyridine, lutidine, collidine, N,N-dimethylaniline, and N,N-diethylaniline; preferred examples thereof include potassium carbonate, potassium hydrogen carbonate, pyridine, triethylamine, and the like; and more preferred examples thereof include potassium carbonate and triethylamine.

The amount of Ar—$CH_2$—$R_4$ (Ar and $R_4$ have the same meanings as those defined above) used is preferably 0.7 to 2.0 equivalents, and more preferably 0.8 to 1.5 equivalents, to the compound represented by formula (B) or formula (B'). When the base is used, the amount of the base used is preferably 1.0 to 10.0 equivalents, and more preferably 1.0 to 5.0 equivalents, to the compound represented by formula (B) or formula (B').

The reaction temperature is preferably in a range from 20° C. to 100° C., and more preferably from 40° C. to 80° C. The reaction time is preferably in a range from 0.1 hours to 3 days, and more preferably in a range from 1 hour to 2 days.

Particularly preferred conditions are as follows: $R_4$ is a chlorine atom; N,N-dimethylformamide, N-methyl-2-pyrrolidinone, N,N-dimethylacetamide, a mixture solvent of N,N-dimethylformamide with toluene, a mixture solvent of N,N-dimethylformamide with xylene, a mixture solvent of xylene with N-methyl-2-pyrrolidinone, or a mixture solvent of xylene with N,N-dimethylacetamide is used as the solvent; the amount of Ar—$CH_2$—$R_4$ used is 0.8 to 1.5 equivalents to the compound represented by formula (B) or formula (B'); the reaction temperature is 40° C. to 80° C.; the reaction time is 1 hour to 2 days; and potassium carbonate or triethylamine is used as the base in an amount of 1.0 to 5.0 equivalents.

One-Pot Production for Obtaining Compound Represented by Formula (I) or Formula (I') from Compound Represented by Formula (A) or Formula (A') Through Compound Represented by Formula (B) or (B')

When the compound represented by formula (I) or formula (I') is synthesized from the compound represented by formula (A) or formula (A'), the compound represented by formula (I) or formula (I') can be obtained by conducting the subsequent step, without isolation of the compound represented by formula (B) or formula (B').

Specifically, the compound represented by formula (I) or formula (I') can be obtained by a reaction in which the reaction product represented by formula (B) or formula (B') is used as it is or after the excessive reagent is removed under reduced pressure; Ar—$CH_2$—$R_4$ (Ar and $R_4$ have the same meanings as those described above) and the base are added thereto; and a reaction therebetween is allowed to proceed under the above-described conditions.

A preferred example of the method for obtaining the compound represented by formula (I) or formula (I') from the compound represented by formula (A) or formula (A') through the compound represented by formula (B) or formula (B') is a method in which a compound represented by formula (A) or formula (A') is reacted with an acylating agent $R_1COR_2$ by use of an aromatic hydrocarbon-based solvent, an aprotic polar solvent, or a mixture solvent thereof in the absence of a base, to thereby obtain a compound represented by formula (B) or formula (B'); then Ar—$CH_2$—$R_4$, a base, and an aromatic hydrocarbon-based solvent, an aprotic polar organic solvent, or a mixture solvent thereof are added; and a reaction therebetween is allowed to proceed, as it is or while the aromatic hydrocarbon-based solvent is distilled off under reduced pressure, to thereby obtain a compound represented by formula (I) or formula (I').

Production of Compound Represented by Formula (B) or (B') from Compound Represented by Formula (A) or Formula (A') in One-Pot Production Here, the numbers of equivalents of reagents are all the numbers of equivalents to the compound represented by formula (A) or formula (A'). To obtain a compound represented by formula (B) or formula (B') from a compound represented by formula (A) or formula (A'), it is particularly preferable to use $R_1COR_2$ or $CF_3COR_2$ in which $R_2$ is a $CF_3COO$ group, an OEt group, a hydroxyl group, or a chlorine atom.

When $R_2$ is a $CF_3COO$ group (for example, trifluoroacetic anhydride), particularly preferred conditions are as follow: toluene is used as the solvent; the amount of the acylating agent used is 1.0 to 1.5 equivalents, the reaction temperature is −10° C. to 30° C.; the reaction time is 0.5 to 4 hours; and regarding the base, no base is used, or when a base is used, potassium carbonate is used in an amount of 1.0 to 3.0 equivalents. When $R_2$ is an OEt group (ethyl trifluoroacetate), particularly preferred conditions are as follows: N,N-dimethylformamide or a mixture solvent of N,N-dimethylformamide with toluene is used as the solvent; the amount of the acylating agent used is 1.5 to 5.0 equivalents; the reaction temperature is 40 to 80° C.; the reaction time is 2 hours to 2 days; and regarding the base, no base is used, or when abase is used, potassium carbonate or dimethylaminopyridine is used in an amount of 0.01 to 2.0 equivalents.

When $R_2$ is a hydroxyl group (for example, trifluoroacetic acid), particularly preferred conditions are as follows: toluene, N,N-dimethylformamide, xylene, N-methyl-2-pyrrolidinone, N,N-dimethylacetamide, a mixture solvent of N,N-dimethylformamide with toluene, a mixture solvent of N,N-dimethylformamide with xylene, a mixture solvent of xylene with N-methyl-2-pyrrolidinone, or a mixture solvent of xylene with N,N-dimethylacetamide is used as the solvent; and the amount of the acylating agent used is 1.0 to 3.0 equivalents. When thionyl chloride, phosphorus oxychloride, or oxalyl dichloride is used, particularly preferred conditions are as follows: the reagent is used in an amount of 0.3 to 3.0 equivalents; no a base is used; the reaction temperature is −10° C. to 40° C.; and the reaction time is 0.5 hours to 1 day. When phosphorus pentoxide, sulfuric acid, or polyphosphoric acid is used, particularly preferred conditions are as follows: the reagent is used in an amount of 0.5 to 2.0 equivalents; the reaction temperature is −10° C. to 160° C.; and the reaction time is 0.5 hours to 1 day. When N,N'-dicyclohexylcarbodiimide or 1-ethyl-3-(3-dimethylaminopropyl)carbodiimide hydrochloride is used, particularly preferred conditions are as follows: the reagent is used in an amount of 0.5 to 3.0 equivalents; the reaction temperature is −10° C. to 40° C.; triethylamine is used as the base in an amount of 0.5 to 3.0 equivalents; and the reaction time is 0.5 to 1 day. When zinc chloride, copper chloride, magnesium chloride, cobalt chloride, nickel chloride, ferric chloride, aluminum chloride, ferric sulfate, aluminum sulfate, boron trifluoride, or p-toluenesulfonic acid is used, particularly preferred conditions are as follows: the reagent is used in an amount of 0.0001 to 0.5 equivalents; no base is used; the reaction temperature is 80° C. to 160° C.; and the reaction time is 2 hours to 2 days.

When $R_2$ is a chlorine atom (for example, trifluoroacetyl chloride), the conditions are as follows: toluene, N,N-dimethylformamide, N-methyl-2-pyrrolidinone, or a mixture solvent of any of these is used as the solvent; the amount of the acylating agent used is 1.0 to 3.0 equivalents; the reaction temperature is −30° C. to 30° C.; and the reaction time is 0.5 hours to 8 hours. Regarding the base, the following conditions are particularly preferable: no base is used, or when a base is used, potassium carbonate is used in an amount of 1.0 to 3.0 equivalents.

Production of Compound Represented by Formula (I) or (I') from Compound Represented by Formula (B) or Formula (B') in One-Pot Production Conditions particularly preferable for obtaining a compound represented by formula (I) or formula (I') from a compound represented by formula (B) or formula (B') are as follows: $R_4$ is a chlorine atom; N,N-dimethylformamide, N-methyl-2-pyrrolidinone, N,N-dimethylacetamide, a mixture solvent of N,N-dimethylformamide with toluene, a mixture solvent of xylene with N,N-dimethylformamide, a mixture solvent of xylene with N-methyl-2-pyrrolidinone, or a mixture solvent of xylene with N,N-dimethylacetamide is used as the solvent; the amount of Ar—$CH_2$—$R_4$ used is 0.8 to 1.5 equivalents to the compound represented by formula (B) or formula (B'); the reaction temperature is 40° C. to 80° C.; the reaction time is 1 hour to 2 days; and regarding the base, potassium carbonate or triethylamine is used in an amount of 1.0 to 5.0 equivalents.

Step of Producing Compound Represented by Formula (Ia) from Compound Represented by Formula (Ba)

A method for obtaining a compound represented by formula (Ia) from a compound represented by formula (Ba) is as follows. Specifically, the compound represented by formula (Ia) can be obtained reacting the compound represented by formula (Ba) with an acylating agent $R_{1a}COR_{2a}$ ($R_{1a}$ and $R_{2a}$ have the same meanings as those defined above) without a solvent or in a solvent which does not affect the reaction in the presence of or in the absence of a base. Here, the numbers of equivalents of reagents herein are all the numbers of equivalents to the compound represented by formula (Ba).

Examples of usable solvents include aromatic hydrocarbon-based solvents such as toluene, xylene, and ethylbenzene; ester-based solvents such as ethyl acetate and butyl acetate; ether-based solvents such as diethyl ether, diisopropyl ether, tetrahydrofuran, and dioxane; aprotic polar organic solvents such as N,N-dimethylformamide, dimethyl sulfoxide, N,N-dimethylacetamide, N-methyl-2-pyrrolidinone, and acetonitrile; halogen-containing solvents such as dichloromethane and chloroform; hydrocarbon-based solvents such as cyclohexane; ketone-based solvents such as acetone and methyl ethyl ketone; water; and mixture solvents thereof.

Examples of usable bases include inorganic bases such as sodium carbonate, potassium carbonate, sodium hydrogen carbonate, potassium hydrogen carbonate, sodium hydroxide, magnesium hydroxide, calcium hydroxide, lithium hydroxide, and barium hydroxide; organic bases such as 1,8-diazabicyclo[5.4.0]undec-7-ene, 1,5-diazabicyclo[4.3.0]non-5-ene, triethylamine, diisopropylethylamine, pyridine, picoline, and dimethylaminopyridine; and alcoholates such as sodium ethoxide, sodium methoxide, and potassium tert-butoxide. The base does not necessarily need to be used; however, when the reaction is carried out in the presence of a base, the base can be used in an amount of 0.01 to 20.0 equivalents.

Examples of the acylating agent $R_1COR_2$ include trifluoroacetic anhydride, trifluoroacetic acid, ethyl trifluoroacetate, trifluoroacetyl chloride, and mixed acid anhydrides. In addition, these acylating agents may be used alone or in combination of two or more. Of these acylating agents, trifluoroacetic anhydride, trifluoroacetic acid, ethyl trifluoroacetate, or trifluoroacetyl chloride can be preferably used. Moreover, when $R_2$ represents a hydroxyl group, the reaction can be carried out by simultaneously using a reagent such as N,N'-dicyclohexylcarbodiimide, 1-ethyl-3-(3-dimethylaminopropyl)carbodiimide hydrochloride, 1,1'-carbonyldiimidazole, dipyridyl disulfide, diimidazolyl disulfide, 1,3,5-trichlorobenzoyl chloride, 1,3,5-trichlorobenzoyl anhydride, PyBop (registered trademark), PyBrop (registered trademark), phosphorus pentoxide, sulfuric acid, polyphosphoric acid, thionyl chloride, phosphorus oxychloride, oxalyl dichloride, zinc chloride, copper chloride, magnesium chloride, cobalt chloride, nickel chloride, ferric chloride, aluminum chloride, ferric sulfate, aluminum sulfate, boron trifluoride, or p-toluenesulfonic acid. The amount of the acylating agent used is preferably 0.5 to 10.0 equivalents.

The reaction temperature is preferably in a range from −80° C. to 200° C. The reaction time is preferably in a range from 0.1 hours to 7 days.

Preferred modes are as follows:

(1) When $R_2$ represents a trifluoroacetoxy group, specifically when trifluoroacetic anhydride is used as the acylating agent, preferred examples of the solvent include ester-based solvents such as ethyl acetate and butyl acetate; halogen-containing solvents such as dichloromethane and chloroform; and aromatic hydrocarbon-based solvents such as toluene, xylene, and ethylbenzene. Here, toluene is more preferable. The reaction is preferably carried out in the absence of a base; however, when a base is used, preferred examples of the base include sodium carbonate, potassium carbonate, potassium hydrogen carbonate, triethylamine, pyridine, and the like, and potassium carbonate is more preferable. The amount of the acylating agent used is preferably 1.0 to 5.0 equivalents, and more preferably 1.0 to 1.5 equivalents. When a base is used, the amount of the base used is preferably 1.0 to 4.5 equivalents, and more preferably 1.0 to 3.0 equivalents. The reaction temperature is preferably in a range from −20° C. to 50° C., and more preferably from −10° C. to 30° C. The reaction time is preferably in a range from 0.1 hours to 7 days, and more preferably in a range from 0.5 hours to 4 hours.

Particularly preferred conditions are as follows: trifluoroacetic anhydride is used as the acylating agent; toluene is used as the solvent; the amount of the acylating agent used is 1.0 to 1.5 equivalents; the reaction temperature is −10° C. to 30° C.; and the reaction time is 0.5 to 4 hours. Regarding the base, no base is used, or when a base is used, potassium carbonate is used in an amount of 1.0 to 3.0 equivalents.

(2) When $R_2$ represents a $C_{1-6}$ alkyloxy group which may be substituted with a halogen atom or a benzyloxy group whose phenyl group may be substituted with a halogen atom, a methyl group, a cyano group, a nitro group, or a methoxy group, specifically when ethyl trifluoroacetate, methyl trifluoroacetate, or propyl trifluoroacetate is used, particularly preferably when ethyl trifluoroacetate or the like is used, preferred solvents include aprotic polar organic solvents such as N,N-dimethylformamide, dimethyl sulfoxide, N,N-dimethylacetamide, N-methyl-2-pyrrolidinone, and acetonitrile; ether-based solvents such as diethyl ether, diisopropyl ether, tetrahydrofuran, and dioxane; and mixture solvents of any of these solvents with an aromatic hydrocarbon-based solvent such as toluene, xylene, or ethylbenzene; and more preferred solvents include N,N-dimethylformamide, and a mixture solvent of N,N-dimethylformamide with toluene. The reaction is preferably carried out in the absence of a base; however, when a base is used, preferred examples of the base include potassium carbonate, triethylamine, dimethylaminopyridine, and the like, and more preferred examples thereof include potassium carbonate and dimethylaminopyridine. The amount of the acylating agent used is preferably 1.0 to 5.0 equivalents, and more preferably 1.5 to 5.0 equivalents. When a base is used, the amount of the base used is preferably 0.01 to 3.0 equivalents, and more preferably 0.01 to 2.0 equivalents. The reaction temperature is preferably in a range from 20° C. to 100° C., and more preferably from 40° C. to 80° C. The reaction time is preferably in a range from 0.1 hours to 7 days, and more preferably in a range from 1 hour to 2 days.

Particularly preferred conditions are as follows: ethyl trifluoroacetate is used as the acylating agent; N,N-dimethylformamide or a mixture solvent of N,N-dimethylformamide with toluene is used as the solvent; the amount of the acylating agent used is 1.0 to 5.0 equivalents; the reaction temperature is 40° C. to 80° C.; and the reaction time is 2 hours to 2 days. Regarding the base, no base is used, or when a base is used, potassium carbonate or dimethylaminopyridine is used in an amount of 0.01 to 2.0 equivalents.

(3) When $R_2$ represents a $C_{1-6}$ alkylcarbonyloxy group which may be substituted with a halogen atom (provided that a trifluoroacetoxy group is excluded) or a phenylcarbonyloxy group whose phenyl group may be substituted with a halogen atom, a methyl group, a cyano group, a nitro group, or a methoxy group, a specific example thereof is a pivaloyl group. The reaction temperature is preferably in a range from −20° C. to 50° C., and more preferably from −10° C. to 30° C. The reaction time is preferably in a range from 0.1 hours to 7 days, and more preferably in a range from 0.5 hours to 4 hours.

(4) When $R_2$ represents a hydroxyl group, specific examples of the acylating agent include trifluoroacetic acid, difluorochloroacetic acid, trichloroacetic acid, difluoroacetic acid, dichloroacetic acid, dibromoacetic acid, chloroacetic acid, difluoropropionic acid, dichloropropionic acid, 2,2,2-trifluoropropionic acid, pentafluoropropionic acid, difluorocyclopropanecarboxylic acid, and the like. Here, trifluoroacetic acid, trichloroacetic acid, dichloroacetic acid, difluoroacetic acid, difluorochloroacetic acid, chloroacetic acid, and pentafluoropropionic acid are preferable; trifluoroacetic acid, difluoroacetic acid, difluorochloroacetic acid, and pentafluoropropionic acid are more preferable; and trifluoroacetic acid is particularly preferable. When trifluoroacetic acid is used, preferred examples of the solvent include aromatic hydrocarbon-based solvents such as toluene, xylene, and ethylbenzene; and aprotic polar organic solvents such as N,N-dimethylformamide, dimethyl sulfoxide, N,N-dimethylacetamide, N-methyl-2-pyrrolidinone, and acetonitrile. Here, toluene, xylene, N,N-dimethylformamide, N-methyl-2-pyrrolidinone, a mixture solvent of toluene with N,N-dimethylformamide, a mixture solvent of xylene with N,N-dimethylformamide, or a mixture solvent of xylene with N-methyl-2-pyrrolidinone is more preferable. Examples of the reagent used simultaneously include N,N'-dicyclohexylcarbodiimide, 1-ethyl-3-(3-dimethylaminopropyl)carbodiimide hydrochloride, phosphorus pentoxide, sulfuric acid, polyphosphoric acid, thionyl chloride, phosphorus oxychloride, oxalyl dichloride, and the like. The reagent is preferably used in an amount of 0.2 to 5.0 equivalents. In addition, when zinc chloride, copper chloride, magnesium chloride, cobalt chloride, nickel chloride, ferric chloride, aluminum chloride, ferric sulfate, aluminum sulfate, boron trifluoride, p-toluenesulfonic acid, or the like is used as the reagent used simultaneously, the reagent is preferably used in an amount of 0.0001 to 1.0 equivalents. The reaction is preferably carried out in the absence of a base, when phosphorus pentoxide, sulfuric acid, polyphosphoric acid, thionyl chloride, phosphorus oxychloride, oxalyl dichloride, zinc chloride, copper chloride, magnesium chloride, cobalt chloride, nickel chloride, ferric chloride, aluminum chloride, ferric sulfate, aluminum sulfate, boron trifluoride, or p-toluenesulfonic acid is used. Meanwhile, The reaction is preferably carried out in the presence of a base, when N,N'-dicyclohexylcarbodiimide or 1-ethyl-3-(3-dimethylaminopropyl)carbodiimide hydrochloride is used. When a base is used, preferred examples of the base include sodium carbonate, potassium carbonate, potassium hydrogen carbonate, triethylamine, pyridine, dimethylaminopyridine, and the like. Here, triethylamine is more preferable. The amount of the acylating agent used is preferably 1.0 to 5.0 equivalents, and more preferably 1.0 to 3.0 equivalents. When thionyl chloride, phosphorus oxychloride, or oxalyl dichloride is used, the reagent is preferably used in an amount of 0.2 to 5.0 equivalents, and the reaction temperature is preferably in a range from −30° C. to 80° C., and more preferably −10° C. to 40° C. When phosphorus pentoxide, sulfuric acid, or polyphosphoric acid is used, the reagent is preferably used in an amount of 0.2 to 5.0 equivalents, and the reaction temperature is preferably in a range from −30° C. to 200° C., and more preferably from −10° C. to 160° C. When N,N'-dicyclohexylcarbodiimide or 1-ethyl-3-(3-dimethylaminopropyl)carbodiimide hydrochloride is used, preferred conditions are as follows: the reagent is used in an amount of 0.2 to 5.0 equivalents; the reaction temperature is preferably in a range from −30° C. to 80° C., and more preferably from −10° C. to 40° C.; and triethylamine is used as the base in an amount of 0.2 to 5.0 equivalents. When zinc chloride, copper chloride, magnesium chloride, cobalt chloride, nickel chloride, ferric chloride, aluminum chloride, ferric sulfate, aluminum sulfate, boron trifluoride, or p-toluenesulfonic acid is used, the following conditions are preferable: the reagent is used in an amount of 0.0001 to 1.0 equivalents; the reaction temperature is preferably in a range from 20° C. to 200° C., and more preferably from 80° C. to 160° C. The reaction time is preferably in a range from 0.1 hours to 7 days, and more preferably in a range from 0.5 hours to 2 days.

Particularly preferred conditions are as follows: trifluoroacetic acid is used as the acylating agent; toluene, N,N-dimethylformamide, xylene, N-methyl-2-pyrrolidinone, N,N-dimethylacetamide, a mixture solvent of N,N-dimethylformamide with toluene, a mixture solvent of xylene with N,N-dimethylformamide, a mixture solvent of xylene with N-methyl-2-pyrrolidinone, or a mixture solvent of xylene with N,N-dimethylacetamide is used as the solvent; and the amount of the acylating agent used is 1.0 to 3.0 equivalents. When thionyl chloride, phosphorus oxychloride, or oxalyl dichloride is used, particularly preferred conditions are as follows: the reagent is used in an amount of 0.3 to 3.0 equivalents; no base is used; the reaction temperature is −10° C. to 40° C.; and the reaction time is 0.5 hours to 1 day. When phosphorus pentoxide, sulfuric acid, or polyphosphoric acid is used, particularly preferred conditions are as follows: the reagent is used in an amount of 0.2 to 2.0 equivalents; the reaction temperature is −10° C. to 160° C.; and the reaction time is 0.5 hours to 1 day. When N,N'-dicyclohexylcarbodiimide or 1-ethyl-3-(3-dimethylaminopropyl) carbodiimide hydrochloride is used, particularly preferred conditions are as follows: the reagent is used in an amount of 0.5 to 3.0 equivalents; the reaction temperature is −10° C. to 40° C.; triethylamine is used as a base in an amount of 0.5 to 3.0 equivalents; and the reaction time is 0.5 to 1 day. When zinc chloride, copper chloride, magnesium chloride, cobalt chloride, nickel chloride, ferric chloride, aluminum chloride, ferric sulfate, aluminum sulfate, boron trifluoride, or p-toluenesulfonic acid is used, particularly preferred conditions are as follows: the reagent is used in an amount of 0.0001 to 0.5 equivalents; no base is used; the reaction temperature is 80° C. to 160° C.; and the reaction time is 2 hours to 2 days.

(5) When $R_2$ represents a halogen atom, specifically when trifluoroacetyl chloride or trifluoroacetyl bromide is used, preferably when trifluoroacetyl chloride is used, preferred examples of the solvent include aromatic hydrocarbon-based solvents such as toluene, xylene, and ethylbenzene; halogen-containing solvents such as dichloromethane and chloroform; and aprotic polar organic solvents such as N,N-dimethylformamide, dimethyl sulfoxide, N,N-dimethylacetamide, N-methyl-2-pyrrolidinone, and acetonitrile. Here, toluene, N,N-dimethylformamide, N-methyl-2-pyrrolidinone, or a mixture solvent of any of these is more preferable. The reaction is preferably carried out in the absence of a base; however, when a base is used, preferred examples of the base include sodium carbonate, potassium carbonate, potassium hydrogen carbonate, triethylamine, pyridine, and the like. Here, potassium carbonate is more preferable. The amount of the acylating agent used is preferably 1.0 to 5.0 equivalents, and more preferably 1.0 to 3.0 equivalents. When a base is used, the amount of the base used is preferably 1.0 to 5.0 equivalents, and more preferably 1.0 to 3.0 equivalents. The reaction temperature is preferably in a range from −80° C. to 40° C., and more preferably from −30° C. to 30° C. The reaction time is preferably in a range from 0.1 hours to 7 days, and more preferably in a range from 0.5 hours to 8 hours.

Moreover, when $R_2$ represents a chlorine atom, it is also possible to use $R_1COCl$ generated in advance by simultaneously using trifluoroacetic acid with thionyl chloride, phosphorus oxychloride, oxalic acid dichloride, or the like outside the reaction system in which the reaction of the compound represented by formula (Aa) is carried out.

Particularly preferred conditions are as follows: trifluoroacetyl chloride is used as the acylating agent; toluene, N,N-dimethylformamide, N-methyl-2-pyrrolidinone, or a mixture solvent thereof is used as the solvent; the amount of the acylating agent used is 1.0 to 3.0 equivalents; the reaction temperature is −30° C. to 30° C.; and the reaction time is 0.5 hours to 8 hours. Regarding the base, particularly preferred conditions are as follows: no base is used, or when a base is used, potassium carbonate is used in an amount of 1.0 to 3.0 equivalents.

The compound represented by formula (Ba) can be obtained by the method described in Patent Document 3, or the like. Specifically, in a method for producing a compound represented by formula (Ba) from a compound represented by formula (Aa), the compound represented by formula (Ba) can be obtained by reacting a compound represented by formula (Aa) with a compound represented by formula (Ca) (X, $R_3$, and $R_4$ have the same meanings as those defined above) without a solvent or in a solvent which does not affect the reaction in the presence of or in the absence of a base.

[Chem. 9]

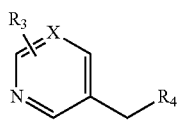

(Ca)

Examples of usable solvents include ether-based solvents such as diethyl ether, diisopropyl ether, tetrahydrofuran, and dioxane; aprotic polar organic solvents such as N,N-dimethylformamide, dimethyl sulfoxide, N,N-dimethylacetamide, acetonitrile, N-methyl-2-pyrrolidinone, N-methyl-2-piperazinone, and N,N-dimethyl-2-imidazolidinone; halogen-containing solvents such as dichloromethane and chloroform; aromatic hydrocarbon-based solvents such as toluene, xylene, and ethylbenzene; and mixture solvents of any of these; and preferred examples thereof include aprotic polar organic solvents. Here, N,N-dimethylformamide, N,N-dimethylacetamide, or toluene is more preferable.

The reaction can be carried out even when no base is used; however, when a base is used, examples of usable bases include inorganic bases such as sodium carbonate, potassium carbonate, sodium hydrogen carbonate, potassium hydrogen carbonate, sodium hydroxide, potassium hydroxide, magnesium hydroxide, calcium hydroxide, lithium hydroxide, and barium hydroxide; and organic bases such as 1,8-diazabicyclo[5.4.0]undec-7-ene, 1,5-diazabicyclo[4.3.0]non-5-ene, triethylamine, diisopropylethylamine, pyridine, lutidine, N,N-dimethylaniline, N,N-diethylaniline, and dimethylaminopyridine; preferred examples thereof include potassium carbonate, triethylamine, pyridine, and the like; and more preferred examples thereof include triethylamine and potassium carbonate.

When a base is used, the amount of the base used is preferably 1.0 to 3.0 equivalents, and more preferably 1.1 to 2.5 equivalents, relative to the compound represented by formula (Aa). The reaction temperature is preferably in a range from −20° C. to 150° C., and more preferably from −10° C. to 100° C.

The reaction time is preferably in a range from 0.1 hours to 7 days, and more preferably from 1 hour to 2 days.

[Chem. 10]

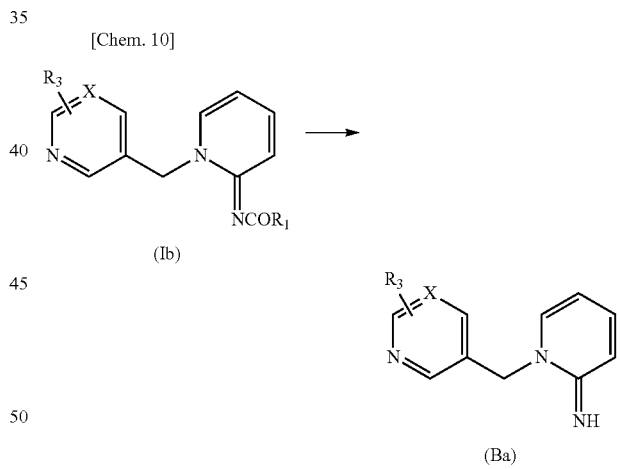

Another example of the method for obtaining the compound represented by formula (Ba) is a method in which a compound represented by formula (Ib) is hydrolyzed, to thereby produce a compound represented by formula (Ba) (in the formula, $R_1$, $R_3$, and X have the same meanings as those defined above).

Examples of usable solvents include ether-based solvents such as diethyl ether, diisopropyl ether, tetrahydrofuran, and dioxane; aprotic polar organic solvents such as N,N-dimethylformamide, dimethyl sulfoxide, N,N-dimethylacetamide, acetonitrile, N-methyl-2-pyrrolidinone, N-methyl-2-piperazinone, and N,N-dimethyl-2-imidazolidinone; halogen-containing solvents such as dichloromethane and chloroform; aromatic hydrocarbon-based solvents such as toluene, xylene, and ethylbenzene; alcohol-based solvents such as methanol and ethanol; water; and mixture solvents of any of these; preferred examples thereof include aromatic hydrocarbon-based solvents, aprotic polar organic solvents, and mixture solvents of water with an alcohol-based solvent. Here, a mixture solvent of water with N,N-dimethylformamide, methanol, or toluene is more preferable. As the acid, a mineral acid such as hydrochloric acid, sulfuric acid, phosphoric acid, or nitric acid can be used. As the base, an inorganic base such as sodium carbonate, potassium carbonate, sodium hydrogen carbonate, potassium hydrogen carbonate, sodium hydroxide, magnesium hydroxide, calcium hydroxide, lithium hydroxide, or barium hydroxide can be used. The reaction temperature is preferably in a range from −20° C. to 150° C., and more preferably from 70° C. to 100° C. The reaction time is preferably in a range from 0.1 hours to 7 days, and more preferably from 1 hour to 8 hours.

When a compound represented by formula (Ia) is synthesized from a compound represented by formula (Aa) through a compound represented by formula (Ba), the compound represented by formula (Ia) can be obtained by conducting the subsequent step, without isolation of the compound represented by formula (Ba).

When a compound represented by formula (I) or formula (Ia) is synthesized from a compound represented by formula (A) or formula (Aa), the compound represented by formula (I) or formula (Ia) can be obtained by a reaction of the acylating agent, the solvent, Ar—CH$_2$—R$_4$, and the base at once.

When a compound represented by formula (I) or formula (Ia) is obtained from a compound represented by formula (A) or formula (Aa) by a reaction using the acylating agent, the solvent, Ar—CH$_2$—R$_4$, and the base at once, a preferred example is as follows. Specifically, a reaction of a compound represented by formula (A) or formula (Aa) is allowed to proceed at 20° C. to 100° C. for 2 hours to 3 days by using an aromatic hydrocarbon-based solvent such as toluene, xylene, or ethylbenzene; an aprotic solvent such as N,N-dimethylformamide, dimethyl sulfoxide, N,N-dimethylacetamide, acetonitrile, or N-methyl-2-pyrrolidinone; or a mixture solvent thereof, an acylating agent in which R$_2$ represents a C$_{1-6}$ alkoxy group which may be substituted with a halogen atom and which is used in an amount of 1.0 to 5.0 equivalents to the compound represented by formula (A) or (Aa), and a base in an amount of 1.0 to 10.0 equivalents to the compound represented by formula (A) or (Aa), and adding Ar—CH$_2$—R$_4$ in an amount of 0.8 to 1.5 equivalents to the compound represented by formula (A) or (Aa), to thereby obtain the compound represented by formula (I) or formula (Ia). Here, specific examples of the acylating agent include ethyl trifluoroacetate, methyl trifluoroacetate, propyl trifluoroacetate, and the like. Moreover, examples of the base used include inorganic bases such as sodium carbonate, potassium carbonate, sodium hydrogen carbonate, potassium hydrogen carbonate, sodium hydroxide, magnesium hydroxide, calcium hydroxide, lithium hydroxide, and barium hydroxide; organic bases such as 1,8-diazabicyclo[5.4.0]undec-7-ene, 1,5-diazabicyclo[4.3.0] non-5-ene, triethylamine, diisopropylethylamine, pyridine, picoline, and dimethylaminopyridine; and alcoholates such as sodium ethoxide, sodium methoxide, and potassium tert-butoxide.

Particularly preferred conditions are as follows: toluene, N,N-dimethylformamide, or a mixture solvent of toluene with N,N-dimethylformamide is used as the solvent; ethyl trifluoroacetate is used as the acylating agent; R$_4$ in Ar—CH$_2$—R$_4$ is a chlorine atom; potassium carbonate is used as the base;

the amount of the acylating agent is preferably 1.0 to 5.0 equivalents, and more preferably 1.5 to 5.0 equivalents, the amount of Ar—CH$_2$—R$_4$ is 0.8 to 1.5 equivalents, and the amount of the base is 1.0 to 5.0 equivalents, relative to the compound represented by formula (I) or formula (Ia); the reaction temperature is 40° C. to 80° C.; and the reaction time is 4 hours to 2 days.

Method for Purifying and Isolating Compound Represented by Formula (I) or Compound Represented by Formula (Ia) from Crude Product The compound represented by formula (I) and the compound represented by formula (Ia) can be purified and isolated by any one of or a combination of crystallization, solvent extraction, column chromatography, and the like, which are ordinarily employed. The solvent used for the solvent extraction is not particularly limited, as long as the solvent is immiscible with water, and specific examples thereof include ethyl acetate, butyl acetate, toluene, ethylbenzene, diethyl ether, diisopropyl ether, dichloromethane, chloroform, and the like. Examples of the solvent used for the crystallization include water, hexane, toluene, acetone, N,N-dimethylformamide, methanol, 2-propanol, dichloromethane, chloroform, ethyl acetate, diethyl ether, xylene, N-methyl-2-pyrrolidinone, N,N-dimethylacetamide, and the like; as well as mixture solvents of any of these.

A preferred method for purifying and isolating the compound represented by formula (I) and the compound represented by formula (Ia) is crystallization. Here, one of or a combination of acetone, toluene, water, N,N-dimethylformamide, methanol, xylene, N-methyl-2-pyrrolidinone, and N,N-dimethylacetamide is preferably used as a crystallization solvent, and combinations of any of water, N,N-dimethylformamide, methanol, N-methyl-2-pyrrolidinone, and N,N-dimethylacetamide are more preferable.

EXAMPLES

Specific examples of the present invention are shown below; however, the present invention is not limited thereto.

Synthesis Example 1

Synthesis of N-[1-((6-Chloropyridin-3-yl)methyl)pyridin-2(1H)-ylidene]-2,2,2-trifluoroacetamide (Compound 1)

(1) In 200 ml of anhydrous dichloromethane, 25 g (270 mmol) of 2-aminopyridine was dissolved, and 41 ml (30 g, 300 mmol) of triethylamine was added thereto, followed by cooling to 0° C. To this mixture, 38 ml (57 g, 270 mmol) of trifluoroacetic anhydride was added dropwise over 15 minutes, followed by stirring at room temperature for 2 hours. After completion of the reaction, the reaction liquid was poured into approximately 100 ml of ice-water, followed by stirring for 10 minutes. The mixture was transferred to a separatory funnel, and phase separation was conducted. The organic layer was washed twice with 150 ml of water, and twice with 150 ml of a 1% aqueous HCL solution, then dried over anhydrous magnesium sulfate, and concentrated under reduced pressure. Thus, 36 g of 2,2,2-trifluoro-N-(pyridin-2(1H)-ylidene)acetamide was obtained (Percentage Yield: 71%).

1H-NMR (CDCl3, δ, ppm):

7.20 (1H, m), 7.83 (1H, m), 8.20 (1H, d), 8.35 (1H, d), 10.07 (1H, brs)

13C-NMR (CDCl3, δ, ppm): 115.3, 115.5 (q), 121.6, 139.1, 147.9, 149.5, 155.3 (q)

MS: m/z=191 (M+H).

(2) In 200 ml of anhydrous acetonitrile, 20 g (126 mmol) of 2-chloro-5-chloromethylpyridine was dissolved. Then, 24 g (126 mmol) of the 2,2,2-trifluoro-N-(pyridin-2(1H)-ylidene)acetamide obtained by the above-described method and 21 g (151 mmol) of potassium carbonate were added to the solution. The mixture was heated under reflux for 6 hours, followed by stirring at room temperature for 10 hours. After completion of the reaction, the reaction liquid was filtered, and the filtrate was concentrated under reduced pressure. Diethyl ether was added to the residue for crystallization. The crystals formed were collected by filtration, and thoroughly washed with diethyl ether and water. The obtained crystals were dried under reduced pressure at 60° C. for 1 hour. Thus, the target substance was obtained. Yield: 26 g (Percentage Yield: 66%).

1H-NMR (CDCl3, δ, ppm):

5.57 (2H, s), 6.92 (1H, td), 7.31 (1H, d), 7.80 (1H, td), 7.87 (1H, dd), 7.99 (1H, dd), 8.48 (2H, m)

13C-NMR (CDCl3, δ, ppm):

53.8, 115.5, 117.2 (q), 122.1, 124.7, 130.0, 139.2, 140.0, 142.5, 149.7, 151.8, 158.9, 163.5 (q)

MS: m/z=316 (M+H).

(3) Powder X-ray crystallography

Powder X-ray diffraction measurement was carried out under the following conditions;

Apparatus name: RINT-2200 (Rigaku Corporation)

X-ray: Cu-Kα (40 kV, 20 mA)

Scan Range: 4 to 40°, Sampling width: 0.02°, Scan rate: 1°/minute

The results are as follows (FIG. 1).

Diffraction angles (2θ): 8.7°, 14.2°, 17.5°, 18.3°, 19.8°, 22.4°, 30.9°, 35.3°.

(4) Differential Scanning calorimetry (DSC)

Differential scanning calorimetry was carried out under the following conditions:

Apparatus name: DSC-60

Sample cell: aluminum

Temperature range: 50° C. to 250° C. (Temperature rise: 10° C./minute)

Figure 2:
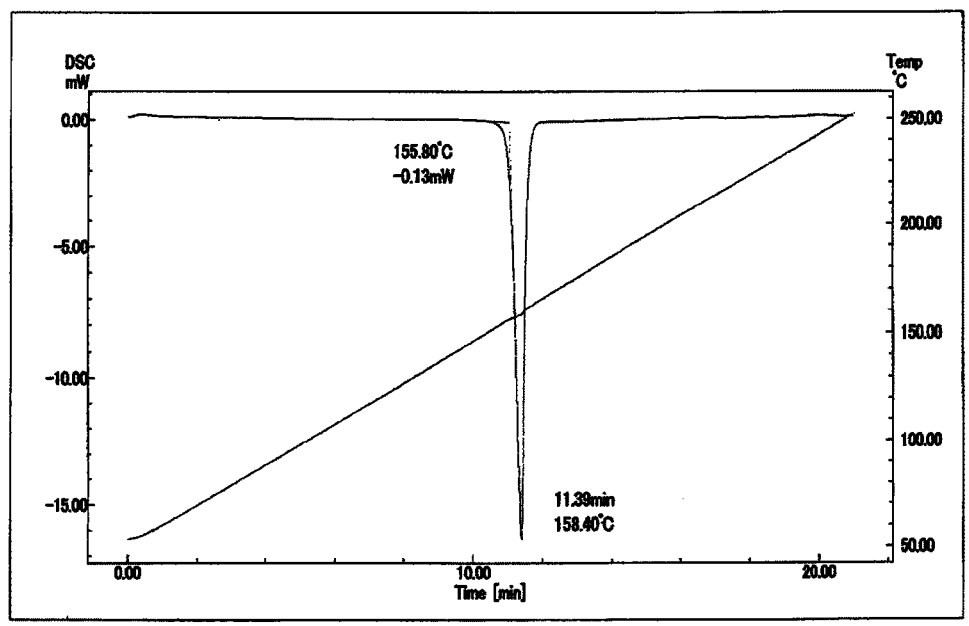
FIG. 2 is a graph showing results of differential scanning calorimetry conducted on crystals of N-[1-((6-chloropyridin-3-yl)methyl)pyridin-2(1H)-ylidene]-2,2,2-trifluoroacetamide prepared by the first production method.

FIG. 2 shows the results.

(5) Moreover, crystals of the same quality were obtained by recrystallization according to the methods (second to fifth production methods) described in the following (i) to (iv). These kinds of crystals were subjected to powder X-ray crystallography and differential scanning calorimetry under the same measurement conditions as described above.

(i) Second Production Method

To Compound 1 (700 mg), approximately 25 ml of hexane and approximately 25 ml of ethyl acetate were added, and Compound 1 was completely dissolved therein by being heated at 65° C. in a hot-water bath. The solution was slowly returned to room temperature, and allowed to stand overnight. The crystals precipitated were collected by filtration, and washed with a small amount of a solution of hexane: ethyl acetate=95:5. The crystals were dried in a desiccator under reduced pressure for 2 hours. Thus, 349 mg of white crystals were obtained.

Figure 3:
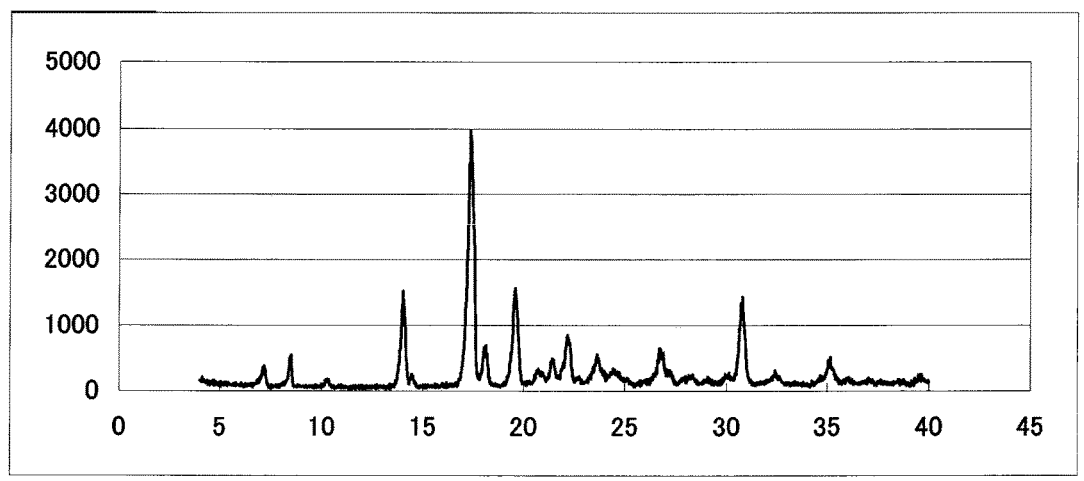
FIG. 3 is a graph showing results of powder X-ray crystallography conducted on crystals of N-[1-((6-chloropyridin-3-yl)methyl)pyridin-2(1H)-ylidene]-2,2,2-trifluoroacetamide prepared by a second production method.

The results of the powder X-ray crystallography are as follows (FIG. 3).

Diffraction angle (2θ): 8.5°, 14.0°, 17.3°, 18.1°, 19.6°, 22.2°, 30.8°, 35.2°

Figure 4:
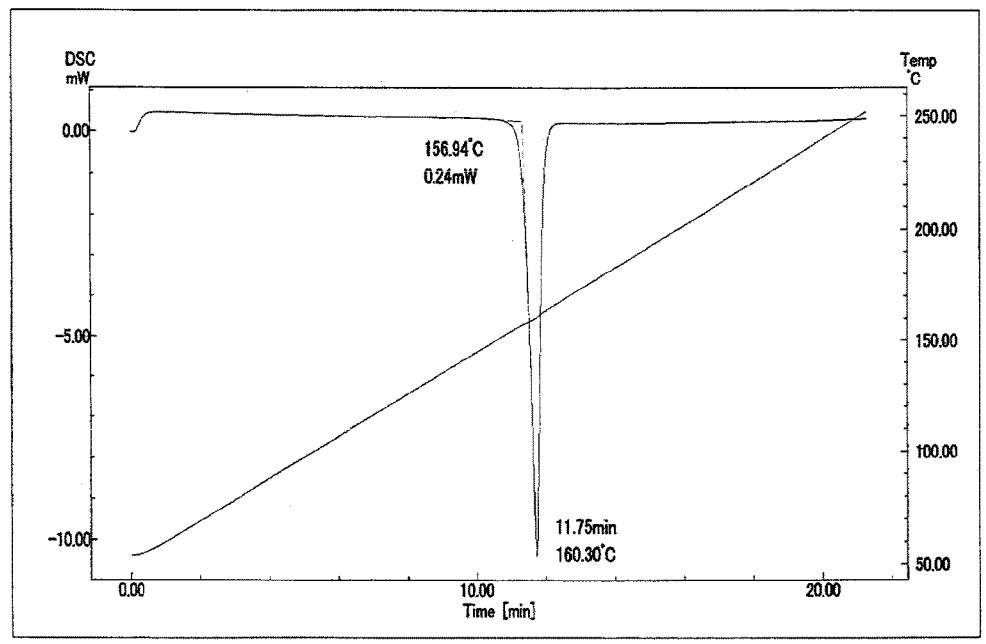
FIG. 4 is a graph showing results of differential scanning calorimetry conducted on crystals of N-[1-((6-chloropyridin-3-yl)methyl)pyridin-2(1H)-ylidene]-2,2,2-trifluoroacetamide prepared by the second production method.

FIG. 4 shows the results of the differential scanning calorimetry.

(ii) Third Production Method

To Compound 1 (1.0 g), 28 ml of 2-propanol was added, and Compound 1 was completely dissolved by being heated at 65° C. in a hot-water bath. The solution was slowly returned to room temperature, and allowed to stand overnight. The crystals precipitated were collected by filtration, then washed with a small amount of 2-propanol, and then dried in a desiccator under reduced pressure for 2 hours. Thus, 695 mg of white crystals were obtained.

Figure 5:
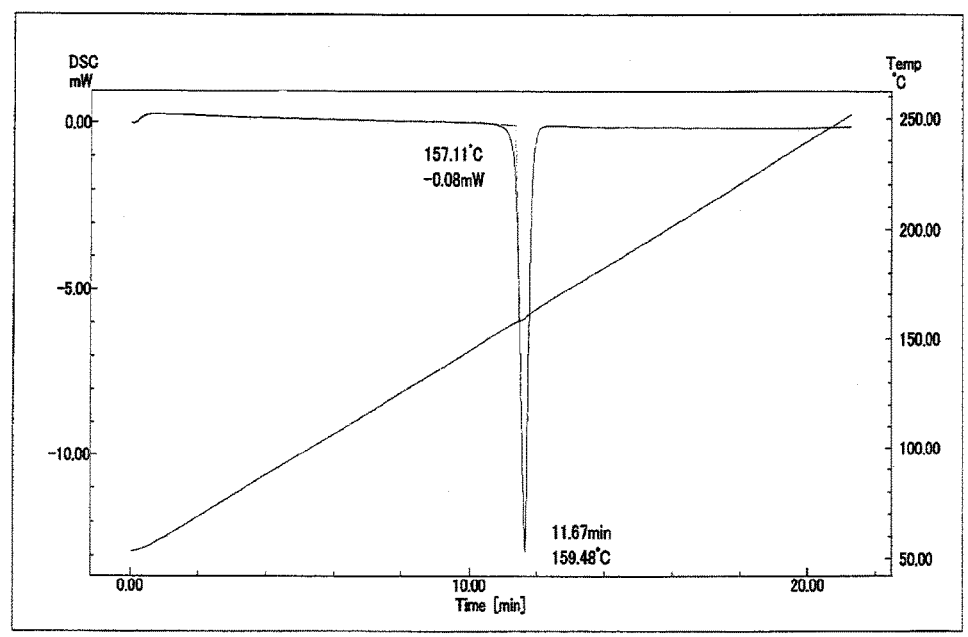
FIG. 5 is a graph showing results of differential scanning calorimetry conducted on crystals of N-[1-((6-chloropyridin-3-yl)methyl)pyridin-2(1H)-ylidene]-2,2,2-trifluoroacetamide prepared by a third production method.

FIG. 5 shows the results of the differential scanning calorimetry.

(iii) Fourth Production Method

To Compound 1 (700 mg), approximately 30 ml of toluene was added, and Compound 1 was completely dissolved by being heated at 65° C. in a hot-water bath. The mixture was slowly returned to room temperature, and allowed to stand overnight. The crystals precipitated were collected by filtration, washed with a small amount of toluene, and then dried in a desiccator under reduced pressure for 2 hours. Thus, 440 mg of white crystals were obtained.

Figure 6:
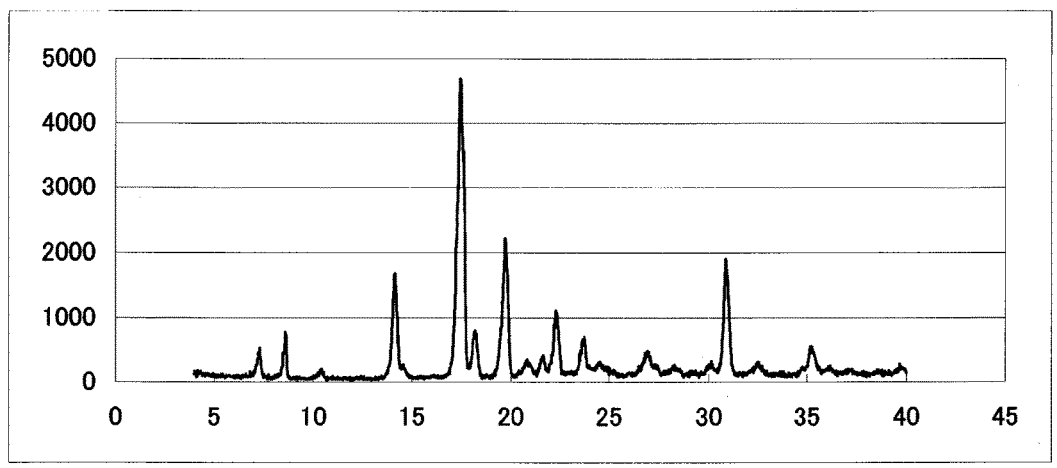
FIG. 6 is a graph showing results of powder X-ray crystallography conducted on crystals of N-[1-((6-chloropyridin-3-yl)methyl)pyridin-2(1H)-ylidene]-2,2,2-trifluoroacetamide prepared by a fourth production method.

The results of the powder X-ray crystallography are as follows (FIG. 6).

Diffraction angle (2θ): 8.6°, 14.2°, 17.5°, 18.3°, 19.7°, 22.3°, 30.9°, 35.3°

Figure 7:
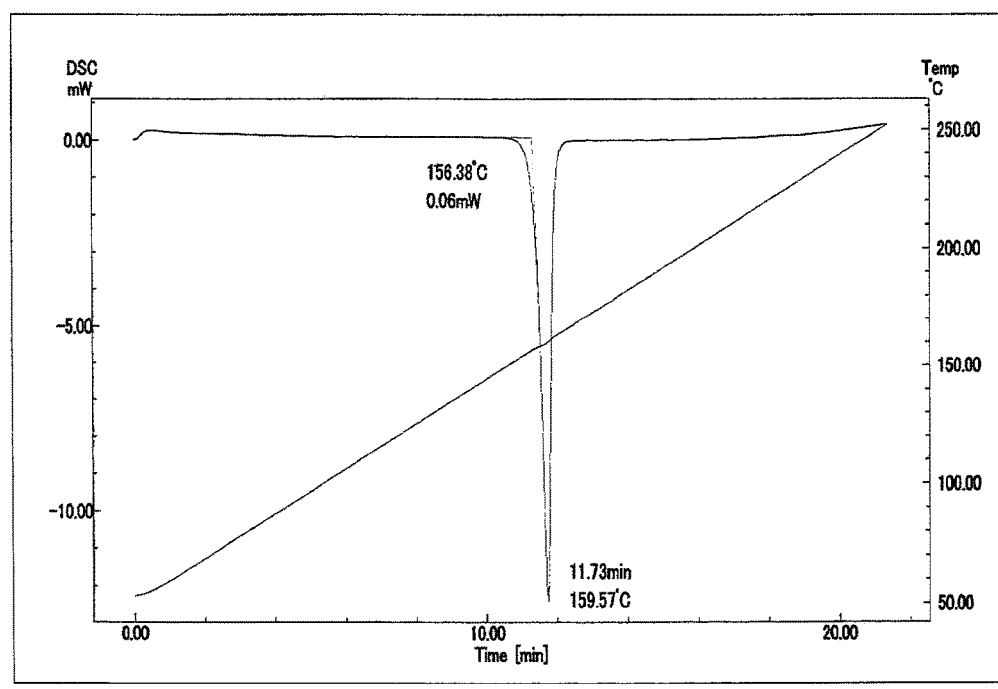
FIG. 7 is a graph showing results of differential scanning calorimetry conducted on crystals of N-[1-((6-chloropyridin-3-yl)methyl)pyridin-2(1H)-ylidene]-2,2,2-trifluoroacetamide prepared by the fourth production method.

FIG. 7 shows the results of the differential scanning calorimetry.

(iv) Fifth Production Method

To Compound 1 (50 mg), approximately 2 ml of methanol and approximately 2 ml of water were added, and Compound 1 was dissolved by being heated at 65° C. in a hot-water bath. This solution was returned to room temperature, and allowed to stand overnight. The crystals precipitated were collected by filtration. Thus, 16 mg of white crystals ware obtained.

Figure 8:
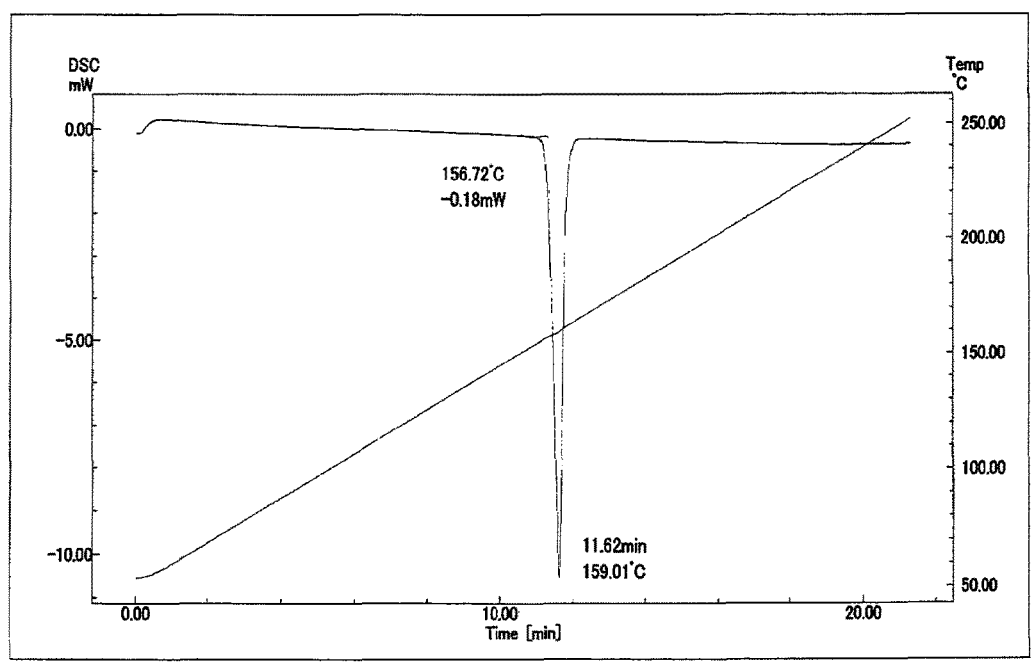
FIG. 8 is a graph showing results of differential scanning calorimetry conducted on crystals of N-[1-((6-chloropyridin-3-yl)methyl)pyridin-2(1H)-ylidene]-2,2,2-trifluoroacetamide prepared by a fifth production method.

FIG. 8 shows the results of the differential scanning calorimetry.

Table 1 shows specific examples of compounds which are pest control agents represented by formula (I), and were produced by methods similar to the method of Synthesis Example 1, and also shows physical properties of the compounds.

TABLE 1

| Comp. No. | Ar | Y | $R_1$ | Yield (%) | $^1$H-HMR (CDCl3, δ, ppm) | MS |
| --- | --- | --- | --- | --- | --- | --- |
| Comp. 9 | 2-chloro-5-thiazolyl | H | CF3 | 54 | 5.61 (2H, s), 6.93 (1H, dd), 7.68 (1H, s), 7.83 (1H, td), 7.97 (1H, d), 8.53 (1H, d) | m/z = 322 (M + H) |
| Comp. 10 | 2-chloro-5-thiazolyl | 4-Cl | CF3 | 62 | 5.58 (2H, s), 6.90 (1H, d), 7.67 (1H, s), 7.90 (1H, d), 8.61 (1H, s) | m/z = 356 (M + H) |

TABLE 1-continued

| Comp. No. | Ar | Y | R₁ | Yield (%) | ¹H-HMR (CDCl3, δ, ppm) | MS |
|---|---|---|---|---|---|---|
| Comp. 11 | 6-chloro-3-pyridyl | 3-Me | CF3 | 58 | 2.31 (3H, s), 5.50 (2H, s), 6.98 (1H, m), 7.34 (1H, d), 7.73 (1H, dd), 7.77 (2H, m), 8.42 (1H, d) | m/z = 330 (M + H) |
| Comp. 12 | 6-chloro-3-pyridyl | 4-Me | CF3 | 78 | 2.40 (3H, s), 5.49 (2H, s), 6.70 (1H, dd), 7.32 (1H, d), 7.70 (1H, d), 7.86 (1H, dd), 8.37 (1H, s), 8.43 (1H, d) | m/z = 330 (M + H) |
| Comp. 13 | 6-chloro-3-pyridyl | 5-Me | CF3 | 68 | 2.29 (3H, s), 5.52 (2H, s), 7.32 (1H, d), 7.62 (1H, s), 7.65 (1H, dd), 7.88 (1H, dd), 8.46 (1H, d), 8.50 (1H, d) | m/z = 330 (M + H) |
| Comp. 14 | 4-chloro-phenyl | H | CF3 | 64 | 5.52 (2H, s), 6.85 (1H, m), 7.30 (2H, d), 7.36 (2H, d), 7.75 (1H, td), 7.84 (1H, d), 8.47 (1H, d) | m/z = 315 (M + H) |
| Comp. 15 | 3-pyridyl | H | CF3 | 78 | 5.57 (2H, s), 6.86 (1H, m), 7.26-7.35 (2H, m), 7.78 (1H, td), 7.86 (1H, m), 8.63 (2H, m), 8.67 1H, d) | m/z = 282 (M + H) |
| Comp. 16 | 6-trifluoromethyl-3-pyridyl | H | CF3 | 74 | 5.62 (2H, s), 6.90 (1H, t), 7.69 (1H, d), 7.81 (1H, t), 7.88 (1H, d), 8.06 (1H, d), 8.56 (1H, d), 8.78 (1H, s) | m/z = 350 (M + H) |
| Comp. 17 | 5,6-dichloro-3-pyridyl | H | CF3 | 59 | 5.49 (2H, s), 6.89 (1H, t), 7.79-7.90 (2H, m), 8.04 (1H, d), 8.37 (1H, d), 8.56 (1H, m) | m/z = 350 (M + H) |
| Comp. 18 | 6-chloro-3-pyridyl | 4-F | CF3 | 42 | 5.52 (2H, s), 6.71 (1H, m), 7.35 (1H, d), 7.86 (1H, dd), 7.94 (1H, m), 8.33 (1H, dd), 8.44 (1H, d) | m/z = 334 (M + H) |
| Comp. 19 | 6-fluoro-3-pyridyl | H | CF3 | 23 | 5.56 (2H, s), 6.89 (1H, td), 6.94 (1H, d), 7.79 (1H, td), 7.87 (1H, d), 8.03 (1H, m), 8.31 (1H, s), 8.54 (1H, d) | m/z = 300 (M + H) |

Synthesis Example 2

Synthesis of 2,2,2-trifluoro-N-(pyridin-2(1H)-ylidene)acetamide

In 10 ml of ethyl acetate, 1.0 g (10.6 mmol) of 2-aminopyridine was dissolved, and 1.78 ml (12.7 mmol) of triethylamine was added thereto. Then, under ice-cooling, 1.62 ml (11.7 mmol) of trifluoroacetic anhydride was added thereto. After that, the mixture was stirred at room temperature for 2 hours, and then 10 ml of ethyl acetate and 10 ml of water were added to this mixture. The resultant mixture was stirred, and then phase separation was conducted. The ethyl acetate layer was further washed twice with 10 ml of water, then dried over anhydrous magnesium sulfate, and concentrated under reduced pressure. Thus, 1.56 g of 2,2,2-trifluoro-N-(pyridin-2(1H)-ylidene)acetamide was obtained (77.2%).

Synthesis Example 3

Synthesis of 2,2,2-Trifluoro-N-(pyridin-2(1H)-ylidene)acetamide

In 25 ml of N,N-dimethylformamide, 4.7 g (50 mmol) of 2-aminopyridine was dissolved, and 35.5 g (250 mmol) of ethyl trifluoroacetate was added thereto. After that, the mixture was stirred at 55 to 60° C. for 15 hours, and then 100 ml of ethyl acetate and 100 ml of water were added thereto. The resultant mixture was stirred, and then phase separation was conducted. The ethyl acetate layer was further washed with 100 ml of water and with 100 mL of aqueous sodium chloride, then dried over anhydrous magnesium sulfate, and concentrated under reduced pressure. Thus, 9.05 g of 2,2,2-trifluoro-N-(pyridin-2(1H)-ylidene)acetamide was obtained (95.6%).

1H-NMR (CDCl3, δ, ppm):
7.20 (1H, ddd), 7.83 (1H, td), 8.20 (1H, d), 8.35 (1H, d), 10.07 (1H, brs).

Synthesis Example 4

Figure 9:
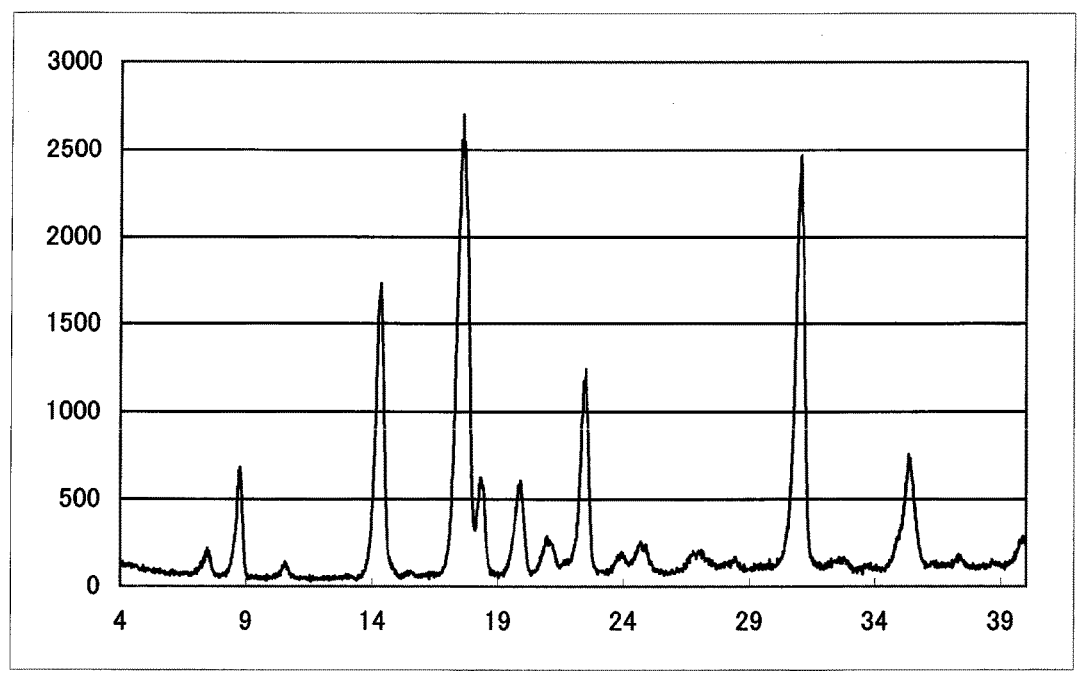
FIG. 9 is a graph showing results of powder X-ray crystallography conducted on crystals of N-[1-((6-chloropyridin-3-yl)methyl)pyridin-2(1H)-ylidene]-2,2,2-trifluoroacetamide synthesized in Synthesis Example 4.

Synthesis of N-[1-((6-chloropyridin-3-yl)methyl) pyridin-2(1H)-ylidene]-2,2,2-trifluoroacetamide In 400 ml of toluene, 50.0 g (0.53 mol) of 2-aminopyridine was dissolved, and then 88.6 ml (0.64 mol) of trifluoroacetic anhydride was added to the mixture dropwise over 30 minutes under cooling to 5° C. After the dropwise addition, the mixture was stirred at room temperature for 30 minutes, and 20 ml of toluene was distilled off under reduced pressure. To the reaction liquid, 250 ml of dimethylformamide was added, and 88.2 g (0.64 mol) of potassium carbonate powder was gradually added to the reaction liquid under ice-cooling. After that, 89.2 g (0.557 mol) of 2-chloro-5-chloromethylpyridine was added to the reaction liquid. Under a reduced pressure (50 to 60 hPa) at 40 to 45° C., toluene was gradually distilled off, and the mixture was heated for 1 hour. Distillation by heating was further conducted at 60 to 70° C. and 35 hPa for 2.5 hours. Then, 5.0 g (0.036 mol) of potassium carbonate powder was added, and water was removed at 50 to 60° C. and 35 hPa for further 1 hour. The reaction liquid was added to 2 L of water of 50° C., and after completion of the addition, the mixture was stirred for 30 minutes. After that, the mixture was filtered, and the crystals were subjected to slurry washing with 200 ml of water and subsequently with 500 ml of water. After the filtration, the crystals were washed with 100 ml of toluene, while being pressed. Further, the crystals were subjected to slurry washing with 400 ml of toluene. The obtained crystals were dried under reduced pressure at 60° C. overnight with a vacuum pump. Thus, 147.78 g of the target compound N-[1-((6-chloropyridin-3-yl)methyl)pyridin-2(1H)-ylidene]-2,2,2-trifluoroacetamide was obtained (88.10). Then, 8.21 g of the obtained title compound was sampled, and dissolved in 100 mL of acetone. To this solution, 300 mL of water was added, and the mixture was stirred at room temperature. The crystals precipitated were collected by filtration, and the obtained crystals were dried under reduced pressure at 60° C. overnight with a vacuum pump. Thus, 7.28 g of crystals were obtained. The results of powder X-ray crystallography conducted on the obtained crystals are as follows (FIG. 9).

Diffraction angles (2θ): 8.8°, 14.3°, 17.6°, 18.3°, 19.9°, 22.5°, 31.0°, 35.4°

Synthesis Example 5

Synthesis of N-[1-((6-Chloropyridin-3-yl)methyl) pyridin-2(1H)-ylidene]-2,2,2-trifluoroacetamide In 250 ml of toluene, 50.0 g (0.53 mol) of 2-aminopyridine was dissolved, and then 88.6 ml (0.64 mol) of trifluoroacetic anhydride was added dropwise over 30 minutes to the solution under cooling to 5° C. After the dropwise addition, the mixture was stirred at room temperature for 30 minutes, and 20 ml of toluene was distilled off under reduced pressure. To the reaction liquid, 250 ml of dimethylformamide was added, and then 88.2 g (0.64 mol) of potassium carbonate powder was added gradually to the reaction liquid under ice-cooling. After that, 87.0 g (0.54 mol) of 2-chloro-5-chloromethylpyridine was added, and toluene was gradually distilled off under a reduced pressure (50 to 60 hPa) at 50 to 60° C., followed by heating at 35 hPa. One hour later, 5.0 g (0.036 mol) of potassium carbonate powder was added, and water was removed at 50 to 60° C. and 35 hPa. Four hours later, the reaction liquid was added to 1.1 L of water of 50° C. The reaction vessel was washed with 150 ml of methanol, and the washing liquid was also added to the water. After the completion of the addition, the mixture was heated at 50° C. for 10 minutes, cooled gradually, and stirred at 15 to 20° C. for 30 minutes. Then, the crystals were filtered, and washed with 150 ml of water, and subsequently with 150 ml of toluene. The obtained crystals were dried under reduced pressure at 60° C. for 11 hours with a vacuum pump. Thus, 147.32 g of the target compound N-[1-((6-chloropyridin-3-yl)methyl)pyridin-2(1H)-ylidene]-2,2,2-trifluoroacetamide was obtained (87.8%).

Synthesis Example 6

Synthesis of N-[1-((6-Chloropyridin-3-yl)methyl) pyridin-2(1H)-ylidene]-2,2,2-trifluoroacetamide In 10 ml of toluene, 1.0 g (10.6 mmol) of 2-aminopyridine was dissolved. After the solution was cooled to 5° C., 1.18 ml (15.9 mmol) of trifluoroacetic acid and 0.99 ml (10.6 mmol) of phosphorus oxychloride were added thereto, followed by stirring at room temperature for 6.5 hours. To the reaction liquid, 5.0 ml of dimethylformamide, 5.87 g (42.5 mmol) of potassium carbonate powder, and 1.72 g (10.6 mmol) of 2-chloro-5-chloromethylpyridine were added, and distillation was conducted under reduced pressure (60 to 35 hPa) at 50 to 60° C. Two and a half hours later, the reaction liquid was added to 100 ml of water, and the crystals were filtered, and washed with 30 ml of water and 15 ml of toluene. The obtained crystals were dried under reduced pressure at 60° C. Thus, 2.09 g of the target compound N-[1-((6-chloropyridin-3-yl)methyl)pyridin-2(1H)-ylidene]-2,2,2-trifluoroacetamide was obtained (62.30).

Synthesis Example 7

Synthesis of N-[1-((6-Chloropyridin-3-yl)methyl) pyridin-2(1H)-ylidene]-2,2,2-trifluoroacetamide In 100 ml of toluene, 10.0 g (0.106 mol) of 2-aminopyridine was dissolved. After the solution was cooled to 5° C., 11.8 ml (0.159 mol) of trifluoroacetic acid and 9.9 ml (0.106 mol) of phosphorus oxychloride were added, followed by stirring at room temperature overnight. Then, 20 ml of toluene was distilled off under reduced pressure. To the reaction liquid, 50 ml of dimethylformamide, 35.28 g (0.256 mol) of potassium carbonate powder, and 17.22 g (0.106 mol) of 2-chloro-5-chloromethylpyridine were added under ice-cooling. Then, distillation was conducted under reduced pressure (60 to 35 hPa) at 50 to 60° C. Two hours later, 25 ml of dimethylformamide, 20 ml of toluene, and 7.35 g (0.053 mol) of potassium carbonate powder were further added, and then distillation was conducted under reduced pressure (60 to 35 hPa) at 50 to 60° C. for 2 hours. To the reaction liquid, 60 ml of methanol and 50 ml of water were added, and the reaction liquid was added to 300 ml of water, while the vessel was also washed. Thirty minutes later, the crystals were filtered, and washed with 70 ml of water and 40 ml of toluene. The obtained crystals were dried under reduced pressure at 60° C. Thus, 25.75 g of the target compound was obtained (76.9%).

Synthesis Example 8

Synthesis of N-[1-((6-Chloropyridin-3-yl)methyl) pyridin-2(1H)-ylidene]-2,2,2-trifluoroacetamide In 100 ml of toluene, 10.0 g (0.106 mol) of 2-aminopyridine was dissolved. After the solution was cooled to 5° C., 11.8 ml (0.159 mol) of trifluoroacetic acid and 7.7 ml (0.106 mol) of thionyl chloride were added thereto, followed by stirring at room temperature overnight. Then, 20 ml of toluene was distilled off under reduced pressure. To the reaction liquid, 50 ml of dimethylformamide, 35.28 g (0.256 mol) of potassium carbonate powder, and 17.22 g (0.106 mol) of 2-chloro-5-chloromethylpyridine were added under ice-cooling. Then, distillation was conducted under reduced pressure (36 hPa) at 50 to 60° C. for 1 hour. To the reaction liquid, 60 ml of methanol and 50 ml of water were added, and the reaction liquid was added to 300 ml of water, while the vessel was also washed. Thirty minutes later, the crystals were filtered, and washed with 70 ml of water and 40 ml of toluene. The obtained crystals were dried under reduced pressure at 60° C. Thus, 22.31 g of the target compound was obtained (66.6%).

Synthesis Example 9

Synthesis of N-[1-((6-Chloropyridin-3-yl)methyl) pyridin-2(1H)-ylidene]-2,2,2-trifluoroacetamide In 50 ml of toluene, 5.0 g (0.053 mol) of 2-aminopyridine was dissolved, and 8.86 ml (0.064 mol) of trifluoroacetic anhydride was added dropwise thereto over minutes under cooling to 5° C. After the dropwise addition, the mixture was stirred at room temperature for 30 minutes, and 10 ml of toluene was distilled off under reduced pressure. To the reaction liquid, 25 ml of dimethylformamide was added, and then 8.82 g of potassium carbonate powder was gradually added thereto under ice-cooling. After that, 11.78 g (0.053 mol) of 2-chloro-5-methanesulfonyloxymethylpyridine was added, and toluene was gradually distilled off under reduced pressure (50 to 60 hPa) at 50 to 60° C., followed by heating at 35 hPa. Thirty minutes later, 30 ml of dimethylformamide, 30 ml of toluene, and 1.18 g (0.0053 mol) of 2-chloro-5-methanesulfonyloxymethylpyridine were added, and reduced pressure distillation was conducted at 50 to 60° C. and 55 hPa. Four hours later, the reaction liquid was added to 250 ml of water. Then, the reaction vessel was washed with 30 ml of methanol and 20 ml of water, and the washing liquids were also added to the water. After completion of the addition, the mixture was stirred at room temperature for 30 minutes. Then, the crystals were filtered, and washed with 50 ml of water, and subsequently with 40 ml of toluene. The obtained crystals were dried under reduced pressure at 80° C. for 11 hours with a vacuum pump. Thus, 11.63 g of the target compound N-[1-((6-chloropyridin-3-yl)methyl)pyridin-2(1H)-ylidene]-2,2,2-trifluoroacetamide was obtained (69.4%).

Synthesis Example 10

Synthesis of N-[1-((6-Chloropyridin-3-yl)methyl)pyridin-2(1H)-ylidene]-2,2,2-trifluoroacetamide In 100 ml of toluene, 10.0 g (0.106 mol) of 2-aminopyridine was dissolved. After the solution was cooled to 5° C., 11.84 ml (0.159 mol) of trifluoroacetic acid and subsequently 5.94 ml (0.064 mol) of phosphorus oxychloride were added thereto, followed by stirring at room temperature overnight. Then, 20 ml of toluene was distilled off under reduced pressure. To the reaction liquid, 50 ml of dimethylformamide, 22.03 g (0.16 mol) of potassium carbonate powder, and 17.56 g (0.108 mol) of 2-chloro-5-chloromethylpyridine were added under ice-cooling. Then, distillation was conducted under reduced pressure (60 to 35 hPa) at 50 to 60° C. One hour later, 20 ml of dimethylformamide, 20 ml of toluene, and 4.41 g (0.032 mol) of potassium carbonate powder were further added thereto, and distillation was conducted under reduced pressure (60 to 35 hPa) and 50 to 60° C. for 1.5 hours. The reaction liquid to which 30 ml of methanol was added was added to 250 ml of water of 50° C. Then, 50 ml of water was added thereto, while the vessel was also washed therewith. After being cooled to room temperature, the mixture was stirred for 30 minutes. The crystals were filtered, and washed with 50 ml of water and 30 ml of toluene. The obtained crystals were dried under reduced pressure at 60° C. Thus, 23.69 g of the target compound was obtained (70.6%).

Synthesis Example 11

Synthesis of N-[1-((6-Chloropyridin-3-yl)methyl)pyridin-2(1H)-ylidene]-2,2,2-trifluoroacetamide In 100 ml of toluene, 10.0 g (0.106 mol) of 2-aminopyridine was dissolved. After the solution was cooled to 5° C., 11.8 ml (0.159 mol) of trifluoroacetic acid and subsequently 7.76 ml (0.106 mol) of thionyl chloride were added thereto portionwise, followed by stirring at room temperature overnight. Then, 50 ml of toluene was distilled off under reduced pressure. To the reaction liquid, 50 ml of toluene was added. Then, 50 ml of dimethylformamide, 22.03 g (0.16 mol) of potassium carbonate powder, and 17.56 g (0.108 mol) of 2-chloro-5-chloromethylpyridine were added thereto under ice-cooling. Then, distillation was conducted under reduced pressure (90 to 36 hPa) at 60° C. for 1.5 hours. To the reaction liquid, 30 ml of methanol and 20 ml of water were added. The reaction liquid was added to 300 ml of water of 50° C., while the vessel was also washed. The mixture was stirred at room temperature for 30 minutes, and then the crystals were filtered, and washed with 50 ml of water and 30 ml of toluene. The obtained crystals were dried under reduced pressure at 60° C. Thus, 21.45 g of the target compound was obtained (64.1%).

Synthesis Example 12

Synthesis of N-[1-((6-Chloropyridin-3-yl)methyl)pyridin-2(1H)-ylidene]-2,2,2-trifluoroacetamide In 500 mL of dimethylformamide, 94 g (1 mol) of 2-aminopyridine was dissolved, and 284 g (2 mol) of ethyl trifluoroacetate was added thereto, followed by stirring at 55 to 60° C. for 24 hours. To the reaction liquid, 82.8 g (0.6 mol) of potassium carbonate powder, 153.9 g (0.95 mol) of 2-chloro-5-chloromethylpyridine, and 300 mL of toluene were added, followed by stirring under reduced pressure (36 hPa) at 50 to 60° C. for 3 hours. To the reaction liquid, 200 mL of methanol was added. Then, the reaction liquid was added to 2 L of hot water of 50° C. After being cooled to room temperature, the mixture was stirred for 3 hours. The crystals were filtered, and washed with 400 mL of water and 450 mL of toluene. The obtained crystals were dried under reduced pressure at 45° C. Thus, 228.9 g of the target compound was obtained (Percentage Yield: 72.7%).

Synthesis Example 13

Synthesis of N-[1-((6-Chloropyridin-3-yl)methyl)pyridin-2(1H)-ylidene]-2,2,2-trifluoroacetamide In a mixture solvent of 30 mL of dimethylformamide and 20 ml of toluene, 9.4 g (0.1 mol) of 2-aminopyridine was dissolved, and 28.4 g (0.2 mol) of ethyl trifluoroacetate was added thereto, followed by stirring at 60 to 65° C. for 8 hours. To the reaction liquid, 16.6 g (0.12 mol) of potassium carbonate powder and 16.2 g (0.1 mol) of 2-chloro-5-chloromethylpyridine were added, followed by stirring at 60 to 65° C. for 15 hours. To the reaction liquid, 15 mL of methanol was added, and then the reaction liquid was added to 120 mL of hot water of 50° C. After being cooled to room temperature, the mixture was stirred for 2 hours. The crystals were filtered, and washed with 50 mL of water and 100 mL of toluene. The obtained crystals were dried under reduced pressure at 45° C. Thus, 25.6 g of the target compound was obtained (Percentage Yield: 81.2%).

Synthesis Example 14

Synthesis of N-[1-((6-Chloropyridin-3-yl)methyl)pyridin-2(1H)-ylidene]-2,2,2-trifluoroacetamide To 13.68 g (0.12 mol) of trifluoroacetic acid, 1.5 mL of dimethylformamide was added. Then, 14.28 g (0.12 mol) of thionyl chloride was added to the mixture, which was heated to 65° C. Trifluoroacetyl chloride generated therefrom was bubbled into a solution which was obtained by dissolving 9.4 g (0.1 mol) of 2-aminopyridine in 50 mL of N-methyl-pyrrolidone, and which was cooled to −10° C., and the mixture was stirred for 1 hour. To the reaction liquid, 100 mL of toluene, 48.3 g (0.35 mol) of potassium carbonate powder, and 16.52 g (0.102 mol) of 2-chloro-5-chloromethylpyridine were added, and distillation was conducted under reduced pressure (36 hPa) at 50 to 60° C. for 3 hours. To the reaction liquid, 20 mL of methanol was added, and the mixture was added to 300 ml of water heated to 50° C., while the vessel was also washed. The mixture was stirred at room temperature for 1.5 hours. Then, the crystals were filtered, and washed with 100 mL of water and 150 mL of toluene. The obtained crystals were dried under reduced pressure at 45° C. Thus, 16.8 g of the target compound was obtained (Percentage Yield: 53.3%).

Synthesis Example 15

Synthesis of N-[1-((6-Chloropyridin-3-yl)methyl) pyridin-2(1H)-ylidene]-2,2,2-trifluoroacetamide To 18.24 g (0.16 mol) of trifluoroacetic acid, 8.76 g (0.12 mol) of dimethylformamide was added. While the mixture was heated to 65° C., 12.26 g (0.08 mol) of phosphorus oxychloride was added to this mixture. Trifluoroacetyl chloride generated therefrom was bubbled into a solution which was obtained by dissolving 9.4 g (0.1 mol) of 2-aminopyridine in 80 mL of N-methylpyrrolidinone, and which was cooled to −15° C., and the mixture was stirred for 2 hours. While being cooled to −10° C., the reaction liquid was neutralized by adding 14.9 g (0.22 mol) of sodium ethoxide powder thereto. To this reaction liquid, 13.8 g (0.1 mol) of potassium carbonate powder and 16.2 g (0.1 mol) of 2-chloro-5-chloromethylpyridine were added, and distillation was conducted under reduced pressure (36 hPa) at 50 to 60° C. for 2 hours. To the reaction liquid, 20 mL of methanol was added, and the mixture was added to 400 ml of water heated to 50° C., while the vessel was also washed. After the mixture was stirred at room temperature for 30 minutes, the crystals were filtered, and washed with 100 mL of water and 50 mL of toluene. The obtained crystals were dried under reduced pressure at 45° C. Thus, 22.5 g of the target compound was obtained (Percentage Yield: 71.4%).

Synthesis Example 16

Synthesis of N-[1-((6-Chloropyridin-3-yl)methyl) pyridin-2(1H)-ylidene]-2,2,2-trifluoroacetamide In 20 ml of dimethylformamide, 3.00 g (18.6 mmol) of 2-chloro-5-chloromethylpyridine was dissolved, and 1.75 g (18.6 mmol) of 2-aminopyridine was added thereto, followed by stirring at 80° C. for 8 hours, and at room temperature for 5 hours. After completion of the reaction, dimethylformamide was distilled off under reduced pressure, and acetonitrile was added. As a result, a solid was precipitated. The solid was collected by filtration, thoroughly washed with acetonitrile, and then dried. Thus, 2.07 g of 1-[(6-chloropyridin-3-yl)methyl]pyridine-2(1H)-imine hydrochloride was obtained (Percentage Yield: 44%).

1H-NMR (DMSO-d6, δ, ppm):
5.65 (2H, s), 6.96 (1H, t), 7.23 (1H, m), 7.57 (1H, d), 7.80 (1H, m), 7.91 (1H, m), 8.28 (1H, m), 8.49 (1H, d)

In 5 ml of anhydrous dichloromethane, 50 mg (0.20 mmol) of 1-[(6-chloropyridin-3-yl)methyl]pyridine-2(1H)-imine hydrochloride obtained by the above-described method was suspended. Then, 122 mg (1.00 mmol) of dimethylaminopyridine and 50 mg (0.24 mmol) of trifluoroacetic anhydride were added in this order to the suspension under ice-cooling, followed by stirring at room temperature for 1 hour. After completion of the reaction, the reaction liquid was diluted with dichloromethane, washed with 1% hydrochloric acid, and then dried over anhydrous magnesium sulfate. The dichloromethane was distilled off under reduced pressure. Thus, the target substance was obtained. Yield: 42 mg (Percentage Yield: 67%).

Synthesis Example 17

Synthesis of N-[1-((6-Chloropyridin-3-yl)methyl) pyridin-2(1H)-ylidene]-2,2,2-trifluoroacetamide In 15 mL of N,N-dimethylformamide, 4.6 g (0.02 mol) of 1-((6-chloropyridin-3-yl)methyl)pyridine-2(1H)-imine obtained by being synthesized according to the method of Synthesis Example 16, and then being neutralized was dissolved, and 5.7 g (0.04 mol) of ethyl trifluoroacetate was added thereto. After stirring at 56° C. overnight, 60 mL of water was added to the mixture. The crystals precipitated were collected by filtration. The obtained crystals were dried under reduced pressure at 45° C. Thus, 5.85 g of the target compound was obtained (Percentage Yield: 92.8%).

Synthesis Example 18

Synthesis of N-[1-((6-Chloropyridin-3-yl)methyl) pyridin-2(1H)-ylidene]-2,2,2-trifluoroacetamide In 6 mL of N,N-dimethylformamide, 2.2 g (0.01 mol) of 1-((6-chloropyridin-3-yl)methyl)pyridine-2(1H)-imine obtained by being synthesized according to the method of Synthesis Example 16, and then being neutralized was dissolved. Then, 828 mg (0.006 mol) of potassium carbonate and 2.52 g (0.012 mol) of trifluoroacetic anhydride were added to the solution under ice-cooling. After stirring at room temperature for 1 hour, 30 mL of water was added to the mixture. The crystals precipitated were collected by filtration. The obtained crystals were washed with 20 mL of water, and dried under reduced pressure at 45° C. Thus, 2.38 g of the target compound was obtained (Percentage Yield: 75.6%).

Synthesis Example 19

Synthesis of N-[1-((6-Chloropyridin-3-yl)methyl) pyridin-2(1H)-ylidene]-2,2,2-trifluoroacetamide To 4.56 g (0.04 mol) of trifluoroacetic acid, 3 mL of N,N-dimethylformamide was added. Then, 3.12 g (0.02 mol) of phosphorus oxychloride was added to the mixture, which was heated to 60° C. Trifluoroacetyl chloride generated therefrom was bubbled into a solution obtained by dissolving, in 25 mL of N-methyl-2-pyrrolidinone, 4.38 g (0.02 mol) of 1-((6-chloropyridin-3-yl)methyl)pyridine-2 (1H)-imine, which was obtained by being synthesized according to the method of Synthesis Example 16, and then being neutralized, and the reaction was allowed to proceed at −10° C. for 45 minutes. Crystals precipitated by adding 125 mL of water were collected by filtration. The obtained crystals were dried under reduced pressure at 45° C. Thus, 2.58 g of the target compound was obtained (Percentage Yield: 40.9%).

Synthesis Example 20

Synthesis of N-[1-((6-Chloropyridin-3-yl)methyl) pyridin-2(1H)-ylidene]-2,2,2-trifluoroacetamide In 3 mL of N,N-dimethylformamide, 4.38 g (0.02 mol) of 1-((6-chloropyridin-3-yl)methyl)pyridine-2(1H)-imine, which was obtained by being synthesized according to the method of Synthesis Example 16, and then neutralized, was dissolved. To this solution, 2.7 g (0.024 mol) of trifluoroacetic acid and 2.8 g (0.02 mol) of phosphorus pentoxide were added. The mixture was stirred at 120° C. for 3 hours, and then returned to room temperature. Crystals precipitated by adding 50 mL of water were collected by filtration. The obtained crystals were dried under reduced pressure at 45° C. Thus, 2.12 g of the target compound was obtained (Percentage Yield: 33.7%).

Synthesis Example 21

Synthesis of N-[1-((6-Chloropyridin-3-yl)methyl) pyridin-2(1H)-ylidene]-2,2,2-trifluoroacetamide In 50 mL of dimethylformamide, 9.4 g (0.1 mol) of 2-aminopyridine was dissolved. To this solution, 28.8 g (0.2 mol) of ethyl trifluoroacetate, 16.2 g (0.1 mol) of 2-chloro-5-chloromethylpyridine, and 13.8 g (0.1 mol) of potassium carbonate were added, followed by stirring at 55 to 60° C. for 20 hours. To the reaction liquid, 1.38 g (0.1 mol) of potassium carbonate powder, 3.24(0.02 mol) of 2-chloro-5-chloromethylpyridine, and 5.68 g (0.04 mol) of ethyl trifluoroacetate were further added, followed by stirring at 55 to 60° C. for 6 hours. To the reaction liquid, 40 mL of methanol was added, and then the reaction liquid was added to 300 mL of hot water of 50° C. After being cooled to room temperature, the mixture was stirred for 1 hour. The crystals were filtered, and washed with 100 mL of water and 75 mL of toluene. The obtained crystals were dried under reduced pressure at 45° C. Thus, 24.0 g of the target compound was obtained (Percentage Yield: 76%).

Synthesis Example 22

Synthesis of N-[1-((6-Chloropyridin-3-yl)methyl) pyridin-2(1H)-ylidene]-2,2,2-trifluoroacetamide In 30 mL of dimethylformamide and 20 mL of toluene, 9.4 g (0.1 mol) of 2-aminopyridine was dissolved. To this solution, 28.8 g (0.2 mol) of ethyl trifluoroacetate, 16.2 g (0.1 mol) of 2-chloro-5-chloromethylpyridine, and 16.6 g (0.12 mol) of potassium carbonate were added, followed by stirring at 60 to 65° C. for 18 hours. To the reaction liquid, 15 mL of methanol was added, and then the reaction liquid was added to 120 mL of hot water of 50° C. After being cooled to room temperature, the mixture was stirred for 1 hour. Crystals were filtered, and washed with 50 mL of water and 100 mL of toluene. The obtained crystals were dried under reduced pressure at 45° C. Thus, 23.9 g of the target compound was obtained (Percentage Yield: 75.9%).

Synthesis Example 23

Synthesis of N-[1-((6-Chloropyridin-3-yl)methyl) pyridin-2(1H)-ylidene]-2,2,2-trifluoroacetamide In a mixture solvent of 25 mL of N,N-dimethylformamide and 10 ml of toluene, 4.7 g (0.05 mol) of 2-aminopyridine was dissolved. To the solution, 35.5 g (0.25 mol) of ethyl trifluoroacetate, 9.72 g (0.06 mol) of 2-chloro-5-chloromethylpyridine, and 8.28 g (0.06 mol) of potassium carbonate powder were added, followed by stirring at 65° C. for 18 hours. To the reaction liquid, 10 mL of methanol was added, and then the reaction liquid was added to 150 mL of hot water of 50° C. After being cooled to room temperature, the mixture was stirred for 1 hour. Crystals were filtered, and washed with 50 mL of water and 50 mL of toluene. The obtained crystals were dried under reduced pressure at 45° C. Thus, 13.78 g of the target compound was obtained (Percentage Yield: 87.5%).

Synthesis Example 24

Synthesis of N-[1-((6-Chloropyridin-3-yl)methyl) pyridin-2(1H)-ylidene]-2,2,2-trifluoroacetamide In 30 mL of dimethylformamide and 20 mL of toluene, 9.4 g (0.1 mol) of 2-aminopyridine was dissolved. To this solution, 14.2 g (0.1 mol) of ethyl trifluoroacetate was added, followed by stirring at 60 to 65° C. for 7 hours. Subsequently, 16.2 g (0.1 mol) of 2-chloro-5-chloromethylpyridine and 16.6 g (0.12 mol) of potassium carbonate were added thereto, followed by stirring at 60 to 65° C. for 18 hours. To the reaction liquid, 15 mL of methanol was added. Then the reaction liquid was added to 150 mL of hot water of 50° C., and the mixture was cooled to room temperature. Crystals were filtered, and washed with 50 mL of water and 75 mL of toluene. The obtained crystals were dried under reduced pressure at 60° C. Thus, 20.6 g of the target compound was obtained (Percentage Yield: 65.4%).

Synthesis Example 25

Synthesis of N-[1-((6-Chloropyridin-3-yl)methyl) pyridin-2(1H)-ylidene]-2,2,2-trifluoroacetamide In 30 mL of dimethylformamide and 20 mL of toluene, 9.4 g (0.1 mol) of 2-aminopyridine was dissolved. To the solution, 7.1 g (0.05 mol) of ethyl trifluoroacetate was added, followed by stirring at 60 to 65° C. for 7.5 hours. After concentration under reduced pressure (90 hPa, 40° C.), the residue was cooled on ice, and 20 mL of toluene and 10.5 g (0.05 mol) of trifluoroacetic anhydride were added to the residue, followed by stirring at room temperature for 1 hour. Subsequently, 16.2 g (0.1 mol) of 2-chloro-5-chloromethylpyridine, 20 mL of dimethylformamide, and 16.6 g (0.12 mol) of potassium carbonate were added, followed by stirring under a reduced pressure of 110 hPa at 60 to 65° C. for 4 hours. After concentration under reduced pressure (90 hPa, 50° C.), 25 mL of methanol was added to the reaction liquid, and this mixture was added to 250 mL of hot water of 50° C. The mixture was cooled to room temperature with stirring. Crystals were filtered, and washed with 90 mL of water and 90 mL of toluene. The obtained crystals were dried under reduced pressure at 60° C. Thus, 19.8 g of the target compound was obtained (Percentage Yield: 62.9%).

Synthesis Example 26

Synthesis of N-[1-((6-Chloropyridin-3-yl)methyl) pyridin-2(1H)-ylidene]-2,2,2-trifluoroacetamide In 30 mL of dimethylformamide and 20 mL of toluene, 9.4 g (0.1 mol) of 2-aminopyridine was dissolved. To the solution, 21.3 g (0.15 mol) of ethyl trifluoroacetate was added, followed by stirring at 60 to 65° C. for 7.5 hours. After concentration under reduced pressure (90 hPa, 40° C.), the residue was cooled on ice, and 20 mL of toluene and 10.5 g (0.05 mol) of trifluoroacetic anhydride were added to the residue, followed by stirring at room temperature for 1 hour. Subsequently, 16.2 g (0.1 mol) of 2-chloro-5-chloromethylpyridine, 20 mL of dimethylformamide, and 16.6 g (0.12 mol) of potassium carbonate were added, followed by stirring under a reduced pressure of 110 hPa at 60 to 65° C. for 4 hours. After concentration under reduced pressure (90 hPa, 50° C.), 25 mL of methanol was added to the reaction liquid, and the mixture was added to 250 mL of hot water of 50° C. Then, the mixture was cooled to room temperature with stirring. Crystals were filtered, and washed with 90 mL of water and 90 mL of toluene. The obtained crystals were dried under reduced pressure at 60° C. Thus, 22.68 g of the target compound was obtained (Percentage Yield: 72.0%).

Synthesis Example 27

Synthesis of N-[1-((6-Chloropyridin-3-yl)methyl)pyridin-2(1H)-ylidene]-2,2,2-trifluoroacetamide In 40 ml of xylene, 2.35 g (0.025 mol) of 2-aminopyridine was suspended. To this mixture, 2.85 g (0.025 mmol) of trifluoroacetic acid and 135 mg of ferric chloride hexahydrate were added, and attached a Dean-Stark trap. The mixture was stirred at 150° C. for 16 hours, removing the resulting water by the Dean-Stark trap. After the solution was cooled to 60° C., 4.05 g (0.025 mol) of 2-chloro-5-chloromethylpyridine, 16 mL of dimethylformamide, and 2.42 g (0.0175 mol) of potassium carbonate were added, followed by stirring under a reduced pressure of 60-110 hPa at 60 to 65° C. for 3 hours. Then, 10 mL of methanol was added to the reaction mixture, and this mixture was added to 80 mL of hot water of 50° C. The mixture was cooled to room temperature with stirring. Crystals were filtered, and washed with 20 mL of water and 20 mL of toluene. The obtained crystals were dried under reduced pressure at 60° C. Thus, 6.32 g of the target compound was obtained (Percentage Yield: 80.3%).

Synthesis Example 28

Synthesis of N-[1-((6-Chloro-5-fluoropyridin-3-yl)methyl)pyridin-2(1H)-ylidene]-2,2,2-trifluoroacetamide (Compound 2)

In 80 ml of carbon tetrachloride, 4.00 g (27.6 mmol) of 2-chloro-3-fluoro-5-methylpyridine was dissolved. To this solution, 7.37 g (41.4 mmol) of N-bromosuccinimide and 20 mg of benzoyl peroxide were added, and the mixture was heated under reflux overnight. After completion of the reaction, the reaction liquid was returned to room temperature, and concentrated under reduced pressure. Then, the residue was purified by silica gel column chromatography (hexane:ethyl acetate=19:1). Thus, 3.06 g of 5-(bromomethyl)-2-chloro-3-fluoropyridine was obtained (Percentage Yield: 51%).

1H-NMR (CDCl3, δ, ppm): 4.45 (2H, s), 7.54 (1H, dd), 8.23 (1H, s)

In 5 ml of anhydrous acetonitrile, 50 mg (0.22 mmol) of 5-(bromomethyl)-2-chloro-3-fluoropyridine obtained by the above-described method was dissolved. To this solution, 42 mg (0.22 mmol) of 2,2,2-trifluoro-N-(pyridin-2(1H)-ylidene)acetamide obtained by the above-described method and 36 mg (0.26 mmol) of potassium carbonate were added in this order, followed by heating under reflux for 7 hours. After completion of the reaction, the reaction liquid was returned to room temperature. The insoluble matters were filtered, and the filtrate was concentrated under reduced pressure. To the residue, diethyl ether was added. As a result, a solid was precipitated. The solid was collected by filtration, washed with diethyl ether, and dried in a desiccator under reduced pressure. Thus, the target substance was obtained. Yield: 29 mg (Percentage Yield: 40%).

1H-NMR (CDCl3, δ, ppm): 5.54 (2H, s), 6.89 (1H, td), 7.76 (1H, dd), 7.80 (1H, td), 7.85 (1H, d), 8.29 (1H, d), 8.57 (1H, d)

MS: m/z=334 (M+H)

Synthesis Example 29

Synthesis of N-[1-((6-Bromopyridin-3-yl)methyl)pyridin-2(1H)-ylidene]-2,2,2-trifluoroacetamide (Compound 3)

In 15 ml of carbon tetrachloride, 500 mg (2.92 mmol) of 2-bromo-5-methylpyridine was dissolved. To this solution, 623 mg (3.50 mmol) of N-bromosuccinimide and 10 mg of benzoyl peroxide were added, followed by heating under reflux for 19 hours. After completion of the reaction, the reaction liquid was returned to room temperature, and concentrated under reduced pressure. The residue was purified by silica gel column chromatography (hexane:ethyl acetate=19:1). Thus, 143 mg of 2-bromo-5-bromomethyl-pyridine was obtained (Percentage Yield: 20%).

1H-NMR (CDCl3, δ, ppm): 4.42 (2H, s), 7.47 (1H, d), 7.59 (1H, dd), 8.38 (1H, d)

In 10 ml of anhydrous acetonitrile, 70 mg (0.28 mmol) of 2-bromo-5-bromomethylpyridine obtained by the above-described method was dissolved. To this solution, 54 mg (0.28 mmol) of 2,2,2-trifluoro-N-(pyridin-2(1H)-ylidene)acetamide synthesized by the above-described method and 46 mg (0.34 mmol) of potassium carbonate were added in this order, followed by heating under reflux for 6 hours. After completion of the reaction, the reaction liquid was returned to room temperature. Then, the insoluble matters were filtered, and the filtrate was concentrated under reduced pressure. To the residue, diethyl ether was added. As a result, a solid was precipitated. The solid was collected by filtration, washed with diethyl ether, and then dried in a desiccator under reduced pressure. Thus, the target substance was obtained. Yield: 81 mg (Percentage Yield: 82%).

1H-NMR (CDCl3, δ, ppm): 5.52 (2H, s), 6.88 (1H, t), 7.48 (1H, d), 7.78 (2H, m), 7.84 (1H, d), 8.44 (1H, d), 8.53 (1H, d)

MS: m/z=360 (M+H)

Synthesis Example 30

Synthesis of 2-chloro-N-[1-((6-Chloropyridin-3-yl)methyl)pyridin-2(1H)-ylidene]-2,2-difluoroacetamide (Compound 4)

In 5 ml of dichloromethane, 200 mg (2.13 mmol) of 2-aminopyridine was dissolved. To this solution, 491 mg (2.55 mmol) of EDC-HCl, 311 mg (2.55 mmol) of dimethylaminopyridine, and 187 μl (2.23 mmol, 290 mg) of chlorodifluoroacetic acid were added in this order, followed by stirring overnight. After completion of the reaction, the reaction liquid was diluted with dichloromethane, washed with water and with 1% hydrochloric acid, and then dried over anhydrous magnesium sulfate. Thus, 105 mg of 2-chloro-2,2-difluoro-N-(pyridin-2(1H)-ylidene)acetamide was obtained (Percentage Yield: 24%).

1H-NMR (CDCl3, δ, ppm): 7.19 (1H, dd), 7.82 (1H, m), 8.18 (1H, d), 8.36 (1H, d), 9.35 (1H, br s)

To 68 mg (0.33 mmol) of 2-chloro-2, 2-difluoro-N-(pyridin-2(1H)-ylidene)acetamide synthesized by the above-described method, 53 mg (0.33 mmol) of 2-chloro- 5-chloromethylpyridine dissolved in 6 ml of anhydrous acetonitrile was added. Subsequently, 50 mg (0.36 mmol) of potassium carbonate was added to the mixture, followed by heating under reflux for 1 hour. After completion of the reaction, the reaction liquid was returned to room temperature, and then concentrated under reduced pressure. Diethyl ether was added to the residue. As a result, a solid was precipitated. The solid was collected by filtration, and dried. Thus, the target substance was obtained. Yield: 49 mg (Percentage Yield: 45%).

1H-NMR (CDCl3, δ, ppm): 5.56 (2H, s), 6.92 (1H, t), 7.33 (1H, d), 7.82 (1H, m), 7.91 (1H, dd), 8.02 (1H, d), 8.45 (1H, d), 8.48 (1H, d)

13C-NMR (CDCl3, δ, ppm): 53.8, 115.2, 120.1 (t), 122.1, 124.8, 139.0, 140.0, 142.3, 150.0, 151.9, 159.1, 159.1, 165.8 (t)

MS: m/z=332 (M+H)

Synthesis Example 31

Synthesis of 2,2,2-Trichloro-N-[1-((6-chloropyridin-3-yl)methyl)pyridin-2(1H)-ylidene]acetamide (Compound 5)

In 4 ml of anhydrous dichloromethane, 70 mg (0.27 mmol) of 1-[(6-chloropyridin-3-yl)methyl]pyridine-2 (1H)-imine hydrochloride obtained by the method of Synthesis Example 16 was suspended. To this suspension, 94 μl (0.68 mmol, 68 mg) of triethylamine and 33 μg (0.27 mmol, 49 mg) of trichloroacetyl chloride were added in this order, followed by stirring at room temperature for 1 hour. After completion of the reaction, the reaction was quenched by adding water, and phase separation was conducted by using dichloromethane and water. The organic layer was washed once with water, and twice with 1% hydrochloric acid, then dried over anhydrous magnesium sulfate, and concentrated under reduced pressure. Diethyl ether was added to the residue. As a result, a solid was precipitated. The solid was collected by filtration, and dried. Thus, the target substance was obtained. Yield: 61 mg (Percentage Yield: 62%).

1H-NMR (CDCl3, δ, ppm): 5.59 (2H, s), 6.86 (1H, t), 7.32 (1H, d), 7.78 (1H, td), 7.91 (2H, m), 8.43 (1H, d), 8.50 (1H, d)

MS: m/z=364 (M+H)

Synthesis Example 32

Synthesis of N-[1-((2-Chloropyrimidin-5-yl)methyl)pyridin-2(1H)-ylidene]-2,2,2-trifluoroacetamide (Compound 6)

In 30 ml of carbon tetrachloride, 1.04 g (8.13 mmol) of 2-chloro-5-methylpyrimidine was dissolved. To this solution, 1.73 g (9.75 mmol) of N-bromosuccinimide and 20 mg of benzoyl peroxide were added, followed by heating under reflux for 6 hours. After completion of the reaction, the reaction liquid was returned to room temperature, and concentrated under reduced pressure. Then, the residue was purified by silica gel column chromatography (hexane:ethyl acetate=3:1). Thus, 641 mg of 5-bromomethyl-2-chloropyrimidine was obtained (Percentage Yield: 380).

1H-NMR (CDCl3, δ, ppm): 4.42 (2H, s), 8.66 (2H, s)

In 6 ml of anhydrous acetonitrile, 104 mg (0.50 mmol) of 5-bromomethyl-2-chloropyrimidine obtained by the above-described method was dissolved. To this solution, mg (0.50 mmol) of 2,2,2-trifluoro-N-(pyridin-2(1H)-ylidene)acetamide obtained by the above-described method and 76 mg (0.55 mmol) of potassium carbonate were added, followed by heating under reflux for 1 hour. After completion of the reaction, the reaction liquid was returned to room temperature. The insoluble matters were removed by filtration, and the filtrate was concentrated under reduced pressure. Diethyl ether was added to the residue. As a result, a solid was precipitated. The solid was collected by filtration, washed with diethyl ether, and then dried in a desiccator under reduced pressure. Thus, the target substance was obtained. Yield: 92 mg (Percentage Yield: 58%).

1H-NMR (CDCl3, δ, ppm): 5.54 (2H, s), 6.98 (1H, m), 7.87 (1H, m), 8.18 (1H, m), 8.48 (1H, m), 8.83 (2H, m)

13C-NMR (CDCl3, δ, ppm): 60.0, 115.6, 117.1 (q), 122.1, 127.5, 139.2, 142.9, 158.8, 160.3 (2C), 161.4, 163.8 (q)

MS: m/z=317 (M+H)

Synthesis Example 33

Synthesis of N-[1-((6-Chloropyridin-3-yl)methyl)pyridin-2(1H)-ylidene]-2,2,3,3,3-pentafluoropropanamide (Compound 7)

In 15 ml of anhydrous dichloromethane, 300 mg (3.19 mmol) of 2-aminopyridine was dissolved. To this solution, 919 mg (4.78 mmol) of EDC-HCl, 583 mg (4.78 mmol) of DMAP, and 397 μl (628 mg, 3.83 mmol) of pentafluoropropionic acid were added in this order, followed by stirring at room temperature overnight. After completion of the reaction, the reaction liquid was diluted with dichloromethane, washed once with water, and twice with 1% hydrochloric acid, then dried over anhydrous magnesium sulfate, and concentrated under reduced pressure. Thus, 85 mg of 2,2,3,3,3-pentafluoro-N-(pyridin-2(1H)-ylidene)propanamide was obtained (Percentage Yield: 11%).

To 77 mg (0.32 mmol) of 2,2,3,3,3-pentafluoro-N-(pyridin-2(1H)-ylidene)propanamide obtained by the above-described method, 52 mg (0.32 mmol) of 2-chloro-5-chloromethylpyridine dissolved in 8 ml of anhydrous acetonitrile and 49 mg (0.35 mmol) of potassium carbonate were added, followed by heating under reflux for 11 hours. After completion of the reaction, the reaction liquid was returned to room temperature, and the insoluble matters were filtered. The filtrate was concentrated under reduced pressure. The residue was purified by silica gel column chromatography (hexane:ethyl acetate=1:3). Thus, the target substance was obtained. Yield: 12 mg (Percentage Yield: 10%).

1H-NMR (CDCl3, δ, ppm): 5.56 (2H, s), 6.90 (1H, td), 7.32 (1H, d), 7.79 (2H, m), 7.84 (1H, d), 8.43 (1H, d), 8.56 (1H, d)

MS: m/z=366 (M+H)

Synthesis Example 34

Synthesis of N-[1-((6-Chloropyridin-3-yl)methyl)pyridin-2(1H)-ylidene]-2,2-difluoroacetamide (Compound 8)

In 10 ml of anhydrous dichloromethane, 400 mg (4.26 mmol) of 2-aminopyridine was dissolved. To this solution, 322 μl (490 mg, 5.11 mmol) of difluoroacetic acid, 982 mg (5.10 mmol) of EDC-HCl, and 622 mg (5.11 mmol) of DMAP were added, followed by stirring at room temperature for 61 hours. After completion of the reaction, the reaction liquid was diluted with dichloromethane, and washed once with water, and twice with 1% HCl aq., then dried over anhydrous magnesium sulfate, and concentrated under reduced pressure. Thus, 102 mg of 2,2-difluoro-N-(pyridin-2(1H)-ylidene)acetamide was obtained (Percentage Yield: 14%).

1H-NMR (CDCl3, δ, ppm): 6.03 (1H, t), 7.15 (1H, m), 7.78 (1H, td), 8.20 (1H, d), 8.34 (1H, dd), 8.72 (1H, br s)

In 10 ml of anhydrous acetonitrile, 100 mg (0.58 mmol) of 2,2-difluoro-N-(pyridin-2(1H)-ylidene)acetamide obtained by the above-described method was dissolved. To this solution, 94 mg (0.58 mmol) of 2-chloro-5-chloromethylpyridine dissolved in 5 ml of anhydrous acetonitrile was added, and subsequently 84 mg (0.63 mmol) of potassium carbonate was added thereto, followed by heating under reflux for 140 minutes. After completion of the reaction, the reaction liquid was returned to room temperature, and the insoluble matters were removed by filtration, and the filtrate was concentrated under reduced pressure. Ether was added to the residue. As a result, a solid was precipitated. The solid was collected by filtration, and dried well. Thus, the target substance was obtained. Yield: 63 mg (Percentage Yield: 37%).

1H-NMR (CDCl3, δ, ppm): 5.52 (2H, s), 5.90 (1H, t), 6.79 (1H, td), 7.33 (1H, d), 7.71 (1H, m), 7.77 (1H, dd), 7.85 (1H, dd), 8.45 (1H, d), 8.50 (1H, d)

13C-NMR (DMSO-d6, δ, ppm): 53.0, 111.0 (t), 115.2, 120.7, 124.7, 131.7, 140.6, 141.6, 143.2, 150.4, 150.9, 158.3, 169.4 (t)

MS: m/z=298 (M+H)

Test Example 1

Test for Control of Diamondback Moth (*Plutella xylostella*)

A leaf disk having a diameter of 5.0 cm was cut out from cabbage grown in a pot. Then, a liquid agent prepared to be 50% acetone-water (to which 0.05% Tween20 was added) and to contain 500 ppm of a compound represented by formula (I) was spread over the leaf disk. After the leaf disk was air dried, second instar larvae were released on the leaf disk. After that, the leaf disk was allowed to stand in a thermostatic chamber at 25° C. (16-hour light period and 8-hour dark period). Three days after the release, the insects were observed for their mortality, and the mortality rate was calculated in accordance with the following formula. The test was duplicated.

Mortality rate (%)=[Number of dead insects/(Number of survived insects+Number of dead insects)]×100

Test Example 2

Test for Control of Cotton Aphid (*Aphis gossypii*)

A leaf disk having a diameter of 2.0 cm was cut out from cucumber (*Cucumis sativus* L.) grown in a pot. Then, a liquid agent prepared to be 50% acetone-water (to which 0.05% Tween20 was added) and to contain 500 ppm of a compound represented by formula (I) was spread over the leaf disk. After the leaf disk was air dried, first instar larvae were released on the leaf disk. After that, the leaf disk was allowed to stand in a thermostatic chamber at 25° C. (16-hour light period and 8-hour dark period). Three days after the release, the insects were observed for their mortality, and the mortality rate was calculated in accordance with the following formula. The test was duplicated.

Mortality rate (%)=[Number of dead insects/(Number of survived insects+Number of dead insects)]×100

Test Example 3

Test for Control of *Laodelphax striatellus*

Roots of wheat seedlings 48 hours after seeding were each treated with 200 μL of a liquid agent prepared to be 10% acetone-water, and to contain 100 ppm of a compound represented by formula (I). The agent was absorbed through the roots for 72 hours, and then 10 second instar larvae of *Laodelphax striatellus* were released on each wheat seedling. After that, the wheat seedlings were allowed to stand in a thermostatic chamber at 25° C. (16-hour light period and 8-hour dark period). Four days after the release, the insects were observed for their mortality, and the mortality rate was calculated in accordance with the following formula. The test was duplicated.

Mortality rate (%)=[Number of dead insects/(Number of survived insects+Number of dead insects)]×100

Table 2 shows the results of Test Examples 1 to 3, i.e., specific bioactivities (mortality rates (%)) of pest control agents represented by formula (I).

TABLE 2

| Reference Example Comp. No. | Ar | Y | R1 | Flutella xylostella | Aphis grossypii | Laodelphax striatellus |
|---|---|---|---|---|---|---|
| 1 | 6-chloro-3-pyridyl | H | CF3 | 100 | 100 | 100 |
| 9 | 2-chloro-5-thiazolyl | H | CF3 | 100 | 100 | 100 |
| P-215 | 6-chloro-3-pyridyl | 5-Cl | CF3 | 100 | 80 | 75 |
| P-216 | 6-chloro-3-pyridyl | 5-F | CF3 | 100 | 95 | 100 |
| P-218 | 2-chloro-5-thiazolyl | 5-Cl | CF3 | 100 | 60 | |
| P-219 | 2-chloro-5-thiazolyl | 5-F | CF3 | 80 | 85 | |
| 12 | 6-chloro-3-pyridyl | 4-Me | CF3 | | 100 | 100 |
| 13 | 6-chloro-3-pyridyl | 5-Me | CF3 | | 75 | 75 |
| 14 | 4-chloro-phenyl | H | CF3 | | 90 | |
| 15 | 3-pyridyl | H | CF3 | 60 | 100 | |
| 2 | 6-chloro-5-fluoro-3-pyridyl | H | CF3 | 100 | 100 | 100 |
| 16 | 6-trifluoromethyl-3-pyridyl | H | CF3 | 30 | 95 | 100 |
| 19 | 6-fluoro-3-pyridyl | H | CF3 | 100 | 100 | 100 |
| 17 | 5,6-dichloro-3-pyridyl | H | CF3 | 100 | 100 | |
| 3 | 6-bromo-3-pyridyl | H | CF3 | 100 | 100 | 100 |
| 18 | 6-chloro-3-pyridyl | 4-F | CF3 | | 80 | |
| P-233 | 6-chloro-3-pyridyl | 3-F | CF3 | | 100 | 75 |
| P-234 | 6-chloro-3-pyridyl | H | CHCl2 | 100 | 100 | 100 |
| 5 | 6-chloro-3-pyridyl | H | CCl3 | 100 | 95 | 75 |

TABLE 2-continued

| Reference Example Comp. No. | Ar | Y | R1 | Flutella xylostella | Aphis grossypii | Laodelphax striatellus |
|---|---|---|---|---|---|---|
| P-236 | 6-chloro-3-pyridyl | H | CH2Cl | | 100 | |
| 8 | 6-chloro-3-pyridyl | H | CHF2 | 100 | 100 | 100 |
| 4 | 6-chloro-3-pyridyl | H | CF2Cl | 100 | 100 | 100 |
| P-240 | 6-chloro-3-pyridyl | H | CHClBr | | 100 | 100 |
| P-241 | 6-chloro-3-pyridyl | H | CHBr2 | | 100 | 100 |
| 7 | 6-chloro-3-pyridyl | H | CF2CF3 | 100 | 100 | 100 |
| 6 | 2-chloro-5-pyrimidinyl | H | CF3 | 100 | 100 | 100 |
| P-244 | 6-chloro-3-pyridyl | H | CH2Br | | 100 | 100 |

<Effect Against Insecticide Resistant Pests>

Reference Example Test for Control of *Nilaparvata lugens*

Rice plant seedlings grown in a pot were treated by soil drench with a liquid agent prepared to be 10% acetone-water, and to contain a predetermined concentration of a compound of the present invention. Three days after the treatment, 10 sensitive or resistant strain of second instar larvae of *Nilaparvata lugens* were released on each of the rice plant seedlings. After that, the rice plant seedlings were allowed to stand in a thermostatic chamber at 25° C. (16-hour light period and 8-hour dark period). Three days after the release, the insects were observed for their mortality, and the mortality rate was calculated in accordance with the following formula. The test was duplicated.

Mortality rate (%)=[Number of dead insects/(Number of survived insects+Number of dead insects)]×100

Note that the pests tested were as follows: Insects bred for generations in a room for a long period (sensitive strain), (I) Insects collected in Kumamoto Prefecture in 2007, and bred for generations in a room (field-collected strain: resistant strain), or (II) Insects collected in Fukuoka Prefecture in 2005, and bred for generations in a room (field-collected strain).

As a result, treatments with Compound 1 at 0.05 mg/seedling achieved mortality rates of 100% for all the strains, and treatments with Compound 1 at 0.005 mg/seedling achieved mortality rates of 90% or higher for all the strains. In addition, treatments with Compound 2 at 0.01 mg/seedling achieved mortality rates of 72% for the sensitive strain and 70% for the strain (II). Treatments with Compound 19 at 0.01 mg/seedling achieved mortality rates of 100% for the sensitive strain and 93% for the strain (II). On the other hand, treatments with imidacloprid at 0.05 mg/seedling achieved mortality rates of 100% for the sensitive strain, 40% for the strain (I), and 60% for the strain (II).

These results indicate that Compound 1 has a high insecticidal activity against *Nilaparvata lugens* resistant to imidacloprid.

Reference Example Test for Control of *Laodelphax striatellus*

Rice plant seedlings grown in a pot were treated by soil drench with a liquid agent prepared to be 10% acetone-water, and to contain a predetermined concentration of a compound of the present invention. Three days after the treatment, 10 sensitive or resistant strain of second instar larvae of *Laodelphax striatellus* were released on each of the rice plant seedlings. After that, the rice plant seedlings were allowed to stand in a thermostatic chamber at 25° C. (16-hour light period and 8-hour dark period). Three days after the release, the insects were observed for their mortality, and the mortality rate was calculated in accordance with the following formula. The test was duplicated.

Mortality rate (%)=[Number of dead insects/(Number of survived insects+Number of dead insects)]×100

Note that the pests tested were insects bred for generations in a room for a long period (sensitive strain), and insects collected in Kumamoto Prefecture in 2006, and bred for generations in a room (field-collected strain: resistant strain).

As a result, treatments with Compound 1 at 0.01 mg/seedling achieved mortality rates of 100% for all the strains, treatments with Compound 1 at 0.005 mg/seedling achieved mortality rates of 90% or higher for all the strains. Meanwhile, treatments with Compound 3 at 0.01 mg/seedling achieved mortality rates of 100% for the sensitive strain and 90% for the field-collected strain. On the other hand, treatments with imidacloprid at 0.01 mg/seedling achieved mortality rates of 100% for the sensitive strain and 50% for the field-collected strain. In addition, treatments with fipronil at 0.01 mg/seedling achieved mortality rates of 100% for the sensitive strain and 70% for the field-collected strain.

These results indicate that Compounds 1 and 3 have high insecticidal activities against *Laodelphax striatellus* resistant to imidacloprid and fipronil.

Reference Example In Vitro Metabolism Test of Compound 1 and Imidacloprid Using Crude Enzyme Extraction Liquid of Housefly (*Musca domestica*)

As described in Pest Management Science (2003), 59(3), 347-352, and Journal of Pesticide Science (2004), 29(2), 110-116, imidacloprid is known to be inactivated by oxidative metabolism, which is thought to be one of the mechanisms for the acquisition of the resistance. To investigate effects on insects acquiring such resistance, the following experiment was carried out.

To adult housefly (*Musca domestica*) (0.645 g), 10 ml of a potassium phosphate buffer (pH 7.4, containing 1 mM EDTA) was added, and the adult housefly was sufficiently ground with Physcotron (Nichion Irika Kikai Seisakusho). After that, the ground material was centrifuged under conditions of 10,000 g and 15 minutes. The obtained supernatant was further centrifuged under conditions of 100,000 g and 60 minutes. Thus, precipitates were obtained. The precipitates were dissolved in 1 ml of a potassium phosphate buffer, and this solution was used as a crude enzyme solution. The enzyme extraction operations were all conducted on ice or under a condition of 4° C.

Reagents were mixed with each other at the following ratio in a tube having a capacity of 1.5 mL, and allowed to react with each other at 25° C. for 40 hours. After the reaction, 1 mL of acetone was added to the mixture, followed by stirring. Then, the formed precipitates were removed by centrifugation at 12000 rpm for 5 minutes. The acetone in the supernatant was distilled off, and the residue was injected into a LC/MS for analysis.
The above-described crude enzyme extraction liquid: 300 μL
Solution of Compound 1 in DMSO: 5 μL
Glucose 6-phosphate solution: 5 μL
NADP+ solution: 5 μL
Glucose 6-phosphate dehydrogenase solution: 5 μL
Potassium phosphate buffer (pH 7.4, containing 1 mM EDTA): 180 μL
<Analysis Conditions>
Column: CAPCELL PAK C18 MG
Mobile phase composition:
0 to 3 minutes: 85% water, 5% acetonitrile, 10% aqueous formic acid solution (0.1 v/v %)
3 to 30 minutes: 85→25% water, 5→65% acetonitrile, 10% aqueous formic acid solution (0.1 v/v %)
30.1 to 36 minutes: 90% acetonitrile, 10% aqueous formic acid solution (0.1 v/v %)
Column temperature: 40° C., Flow rate: 0.35 mL/minute,
Injection amount: 100 μL
UV wavelength: 325 nm for Compound 1, 300 nm for imidacloprid.
As a result, the total area percentage of metabolites was 0.08 for Compound 1. In contrast, the total area percentage of metabolites was 2.55 for imidacloprid. The amount of metabolites of Compound 1 was smaller than that of imidacloprid. These results indicate that Compound 1 can be used effectively for pest control of resistant pests which inactivate imidacloprid by metabolism.

<Controlling Effect on Animal-Parasitic Pests>
Reference Example Test for Control of *Haemaphysalis longicornis*

Into a glass vial having a capacity of 4 mL, 30 μL of an acetone solution containing 200 ppm or 10 ppm of a compound of the present invention was introduced. The vial was placed on a shaker, and air dried, while being rotated. Thus, a dry film of the compound was formed on the inner wall of the vial. After the vial was dried for 24 hours or longer, 10 larvae of *Haemaphysalis longicornis* were released in the vial, and then the vial was capped. The vial was allowed to stand in a thermostatic chamber under conditions of 25° C., a humidity of 85%, and total darkness. One day after the release, the larvae were observed for their mortality, and the mortality rate was calculated in accordance with the following formula. The test was duplicated.

Mortality rate (%)=[Number of dead insects/(Number of survived insects+Number of dead insects)]×100

As a result, Compound 1 and Compound 9 in treatment amounts of 200 ppm showed tickcidal effects with mortality rates of 80% or higher.
Compound 1 and Compound 9 in treatment amounts of 10 ppm showed acaricidal effects with mortality rates of 80% or higher.
In a similar test, imidacloprid in a treatment amount of 10 ppm achieved a mortality rate of 4%.
Reference Example Effect of Controlling *Haemaphysalis longicornis* on Body Surface of Mouse Hair on the back of a mouse (ICR, male, 5-weeks old) in a region having a diameter of approximately 2 cm was shaved, and a 15-mL polystyrene conical tube cut to have a height of approximately 1.5 cm was bonded to this region with an instant adhesive.
Then, 20 μL of a 1000-fold diluted liquid of a pest control agent prepared according to the following formulation was added dropwise onto the body surface of the mouse within the bonded tube. After sufficient drying, or more larvae of *Haemaphysalis longicornis* were released into the tube, and the tube was capped. Three days after the release, the larvae of *Haemaphysalis longicornis* were observed for their mortality, and the blood-sucking inhibition rate was calculated in accordance with the following formula.
Formulation [Drop Preparation]
Compound 1 48% by weight
Ethanol 52% by weight
The components were uniformly mixed with each other, and a drop preparation was obtained.

blood-sucking inhibition rate (%)=100−[Number of allodermanyssus/(Number of survived ticks+Number of dead ticks)]×100

As a result, Compound 1 showed an effect of controlling *Haemaphysalis longicornis* with a blood-sucking inhibition rate of 91%.

INDUSTRIAL APPLICABILITY

As described above, according to the present invention, it is possible to produce a 2-acyliminopyridine derivative represented by formula (I), which is useful as a pest control agent, in a good yield and, if necessary, effectively in a one-pot manner, and in turn to provide the 2-acyliminopyridine derivative in an amount required as a tick control agent stably and at a low cost. Accordingly, the present invention greatly contributes to the field of pest control.

What is claimed is:
1. A method for producing a compound represented by the following formula (I):

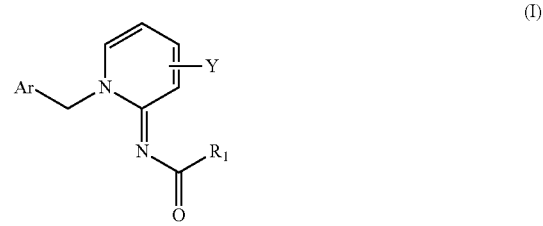

wherein Ar is a 6-chloro-3-pyridyl group, $R_1$ represents an optionally substituted $C_{1-6}$ alkyl group, and Y is a hydrogen atom:
the method comprising, as shown in the following reaction formula:

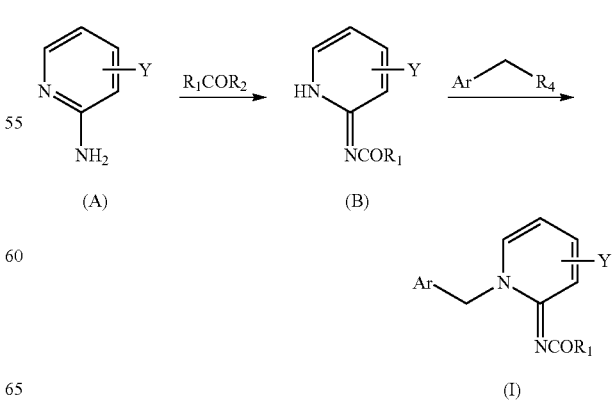

the steps of:

acylating an amino group at position 2 of a compound represented by formula (A), wherein Y is a hydrogen atom, with an acylating agent represented by $R_1COR_2$, wherein $R_1$ represents an optionally substituted $C_{1-6}$ alkyl group, and $R_2$ represents (1) a trifluoroacetoxy group, (2) a $C_{1-6}$ alkyloxy group optionally substituted with a halogen atom or a benzyloxy group, wherein a phenyl group of the benzyloxy group is optionally substituted with a halogen atom, a methyl group, a cyano group, a nitro group, or a methoxy group, (3) a $C_{1-6}$ alkylcarbonyloxy group which is optionally substituted with a halogen atom (provided that a trifluoroacetoxy group is excluded) or a phenylcarbonyloxy group wherein a phenyl group of the phenylcarbonyloxy group is optionally substituted with a halogen atom, a methyl group, a cyano group, a nitro group, or a methoxy group, (4) a hydroxyl group, or (5) a halogen atom; wherein the acylation is carried out in the presence of a base and in the presence or absence of at least one compound selected from the group consisting of a condensation agent, phosphorus pentoxide, sulfuric acid, polyphosphoric acid, thionyl chloride, phosphorus oxychloride, oxalyl dichloride, p-toluenesulfonic acid, boron trifluoride, a metal halide, a metal sulfate, a metal nitrate, and a metal oxide, wherein the metal is iron, cobalt, copper, nickel, zinc, aluminum, lithium, or magnesium; to thereby produce a compound represented by formula (B); and alkylating a nitrogen atom at position 1 of the compound represented by formula (B) with $Ar-CH_2-R_4$; wherein Ar is a 6-chloro-3-pyridyl group, and $R_4$ represents a halogen atom, a $C_{1-6}$ alkylsulfoxy group which is optionally substituted with a halogen atom, or a phenylsulfoxy group which is optionally substituted with a halogen atom or a methyl group.

2. A method for producing a compound represented by the following formula (I):

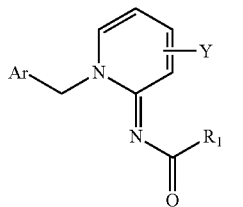

(I)

wherein Ar represents a phenyl group or a pyridyl group, optionally substituted with a halogen atom, an alkyl group or a haloalkyl group; $R_1$ represents a $C_{1-6}$ alkyl group optionally substituted with a halogen atom;

and Y represents a hydrogen atom;

the method comprising combining together at once to form a mixture:

(i) a compound represented by formula (A):

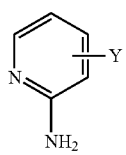

(A)

wherein Y represents a hydrogen atom;

(ii) an acylating agent represented by $R_1COR_2$, wherein $R_1$ represents a $C_{1-6}$ alkyl group optionally substituted with a halogen atom, and $R_2$ represents a trifluoroacetoxy group, an ethoxy group, a hydroxyl group, or chlorine atom;

and (iii) an alkylating agent $Ar-CH_2-R_4$, wherein Ar represents a phenyl group or a pyridyl group, optionally substituted with a halogen atom, an alkyl group or a haloalkyl group and $R_4$ represents a halogen atom, a $C_{1-6}$ alkylsulfoxy group which is optionally substituted with a halogen atom, or a phenylsulfoxy group which is optionally substituted with a halogen atom or a methyl group;

and reacting the mixture, in the presence of a base and in the presence or absence of at least one compound selected from the group consisting of a condensation agent, phosphorus pentoxide, sulfuric acid, polyphosphoric acid, thionyl chloride, phosphorus oxychloride, oxalyl dichloride, p-toluenesulfonic acid, boron trifluoride, a metal halide, a metal sulfate, a metal nitrate, and a metal oxide, wherein the metal is iron, cobalt, copper, nickel, zinc, aluminum, lithium, or magnesium.

3. The method according to claim 1, wherein $R_1$ is a trifluoromethyl group.

4. The method according to claim 1, wherein $R_1$ is a trifluoromethyl group, and $R_2$ is a trifluoroacetoxy group, an ethoxy group, a hydroxyl group, or a chlorine atom.

5. The method according to claim 1, wherein $R_1COR_2$ is at least one acylating agent selected from the group consisting of trifluoroacetic anhydride, trifluoroacetic acid, ethyl trifluoroacetate, trifluoroacetyl chloride, and mixed acid anhydrides, and is used in an amount of 1.0 to 5.0 equivalents to the compound represented by formula (A).

6. The method according to claim 1, wherein $R_1COR_2$ is trifluoroacetic anhydride, and is used in an amount of 1.0 to 1.5 equivalents to the compound represented by formula (A).

7. The method according to claim 1, wherein $R_1COR_2$ is ethyl trifluoroacetate, and is used in an amount of 1.0 to 5.0 equivalents to the compound represented by formula (A).

8. The method according to claim 1, wherein $R_1COR_2$ is trifluoroacetyl chloride, and is used in an amount of 1.0 to 3.0 equivalents to the compound represented by formula (A).

9. The method according to claim 1, wherein $R_1COR_2$ is trifluoroacetic acid, and is used in an amount of 1.0 to 3.0 equivalents to the compound represented by formula (A), wherein the acylation is carried out in the presence of at least one compound selected from the group consisting of thionyl chloride, phosphorus oxychloride, p-toluenesulfonic acid, boron trifluoride, a metal halide, a metal sulfate, a metal nitrate, and a metal oxide, wherein the metal is iron, cobalt, copper, nickel, zinc, aluminum, lithium, or magnesium.

* * * * *